United States Patent
Roberts et al.

(10) Patent No.: US 7,248,351 B2
(45) Date of Patent: Jul. 24, 2007

(54) OPTIMIZING LIGHT PATH UNIFORMITY IN INSPECTION SYSTEMS

(75) Inventors: William Roberts, Mechanicsville, VA (US); Gerhard Kunkel, Dresden (DE); Patrick Lomtscher, Dresden (DE); Karl Schumacher, Radebeul (DE)

(73) Assignee: Infineon Technologies AG, Munich (DE)

( * ) Notice: Subject to any disclaimer, the term of this patent is extended or adjusted under 35 U.S.C. 154(b) by 130 days.

(21) Appl. No.: 11/067,191

(22) Filed: Feb. 25, 2005

(65) Prior Publication Data

US 2006/0192947 A1    Aug. 31, 2006

(51) Int. Cl.
G01N 21/88 (2006.01)
G01B 11/00 (2006.01)

(52) U.S. Cl. ................................ 356/237.1; 356/394

(58) Field of Classification Search ............. 356/237.1, 356/521, 484, 485, 487, 512–513, 499, 490, 356/388–394; 250/548; 359/385; 355/67
See application file for complete search history.

(56) References Cited

U.S. PATENT DOCUMENTS

| | | | | |
|---|---|---|---|---|
| 3,796,498 A | * | 3/1974 | Post | 356/618 |
| 4,079,411 A | * | 3/1978 | Engelbrecht et al. | 396/305 |
| 4,771,180 A | * | 9/1988 | Nomura et al. | 250/548 |
| 5,000,573 A | * | 3/1991 | Suzuki et al. | 356/490 |
| 5,218,423 A | * | 6/1993 | Kishner | 356/513 |
| 5,299,062 A | | 3/1994 | Ogata | |
| 5,333,050 A | * | 7/1994 | Nose et al. | 356/490 |
| 5,386,319 A | * | 1/1995 | Whitney | 359/575 |
| 5,442,480 A | | 8/1995 | Swanson et al. | |
| 5,574,559 A | * | 11/1996 | Kaneda et al. | 356/499 |
| 5,648,951 A | * | 7/1997 | Kato et al. | 369/112.07 |
| 5,666,197 A | * | 9/1997 | Guerra | 356/512 |
| 5,729,383 A | * | 3/1998 | Chastang et al. | 359/385 |
| 5,825,468 A | | 10/1998 | Ishimaru | |
| 6,091,486 A | | 7/2000 | Kirk | |
| 6,160,831 A | * | 12/2000 | Kleinschmidt et al. | 372/57 |
| 6,174,741 B1 | | 1/2001 | Hänsch et al. | |
| 6,577,406 B2 | | 6/2003 | Bruce et al. | |
| 6,606,151 B2 | | 8/2003 | Kunkel et al. | |
| 6,646,729 B2 | | 11/2003 | van der Laan et al. | |
| 6,678,037 B2 | * | 1/2004 | Van Elp et al. | 355/67 |
| 6,842,237 B2 | | 1/2005 | Ausschnitt et al. | |
| 2004/0263836 A1 | | 12/2004 | Eom et al. | |
| 2005/0001180 A1 | | 1/2005 | Lyons | |

OTHER PUBLICATIONS

Kirk, J. "Application of Blazed Gratings for Determination of Equivalent Primary", Proceedings of SPIE, vol. 3679, pp. 70-76, (1999).

* cited by examiner

Primary Examiner—Sang H. Nguyen
(74) Attorney, Agent, or Firm—Dicke, Billig & Czaja, PLLC

(57) ABSTRACT

An inspection system includes an illumination source configured to illuminate a blazed phase grating sample, image collection pathways and an imaging system configured to capture an image of a sample point of the blazed phase grating sample, and a controller configured to adjust the illumination source in response to an analysis of the image of the sample point to determine illumination uniformity of the inspection system.

17 Claims, 16 Drawing Sheets

Fig. 9A 600
Fig. 9B 602
Fig. 9C 604
Fig. 9D 606
Fig. 9E 608
Fig. 9F 610
Fig. 9G 612
Fig. 9H 614
Fig. 9I 616
Fig. 9J 618
Fig. 9K 620
Fig. 9L 622
Fig. 9M 624
Fig. 9N 626
Fig. 9O 628
Fig. 9P 630

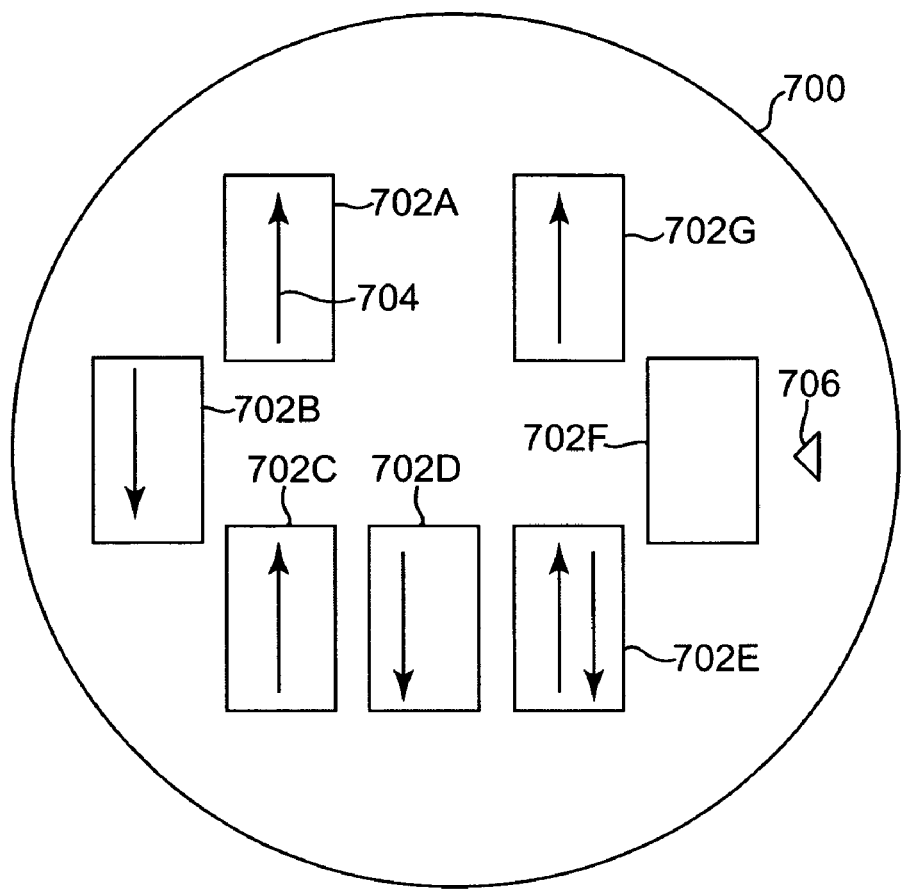
Fig. 10
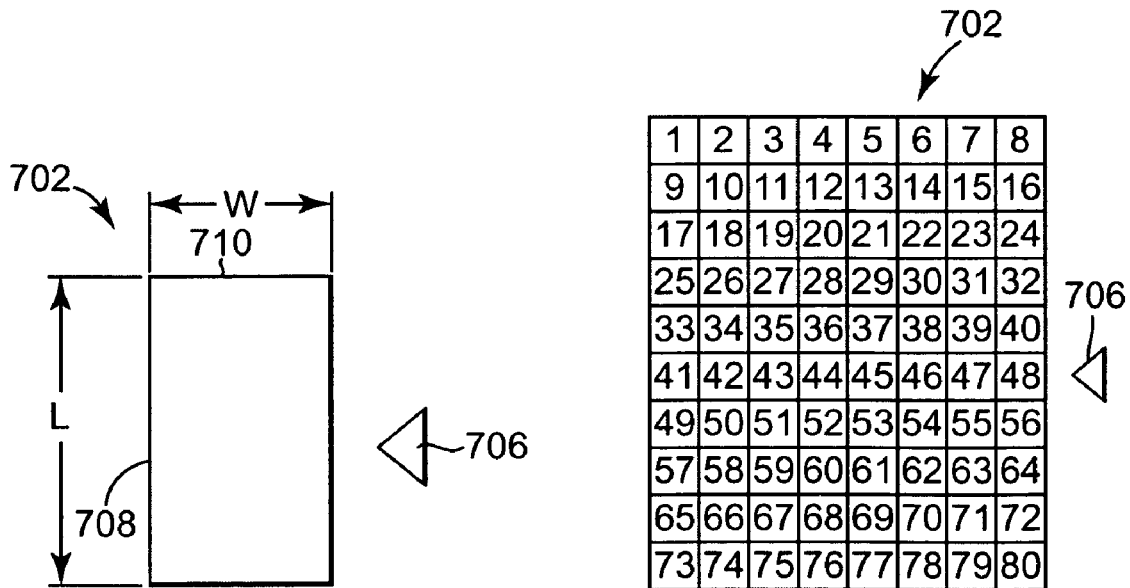
Fig. 11A  Fig. 11B

OPTIMIZING LIGHT PATH UNIFORMITY IN INSPECTION SYSTEMS

CROSS-REFERENCE TO RELATED APPLICATIONS

This application is related U.S. patent application Ser. No. 11/066,638, entitled "SYSTEM FOR ANALYZING IMAGES OF BLAZED PHASE GRATING SAMPLES"; U.S. patent application Ser. No. 11/066,902, entitled "AUTOMATED FOCUS FEEDBACK FOR OPTICAL LITHOGRAPHY TOOL"; U.S. patent application Ser. No. 11/066,913, entitled "OPTIMIZING FOCAL PLANE FITTING FUNCTIONS FOR AN IMAGE FIELD ON A SUBSTRATE;" U.S. patent application Ser. No. 11/065,931, entitled "RUN TO RUN CONTROL FOR LENS ABERRATIONS"; all filed Feb. 25, 2005, and all of which are incorporated herein by reference.

BACKGROUND

Process and device yield in optical lithography imaging processes are directly related to Critical Dimension (CD) uniformity. CD uniformity is dependent on several processes during the optical lithography process, such as imaging, etching, and deposition. In the lithography process, there are several factors that influence the CD uniformity on a wafer, such as reticle uniformity, slit uniformity, wafer flatness, lens aberrations, and imaging focus. Typically, these factors are tested individually using a variety of tests that may be time consuming, require specialized hardware to perform, and/or require technicians who have received specialized training to perform the tests.

Typical methods for determining parameters of an exposure tool, such as scan direction effects, field attributes, and lens system aberrations cannot be performed without severely disrupting the normal manufacturing process on the exposure tool. In addition, the typical methods fail to efficiently and effectively organize and analyze the large amounts of data needed to accurately and precisely determine the parameters.

Typically, projection lenses for exposure tools in the semiconductor industry have adjustable lens elements for correcting for lens aberrations. Correcting for lens aberrations in some tools may be performed by adjusting the position and tilt of elements within the lens system. Tool vendors typically adjust the lens elements during the calibration of the exposure tools. The majority of calibration procedures require a specially trained service or maintenance engineer and specialized hardware to perform. In addition, the calibration procedures are usually time consuming requiring significant downtime on the exposure tool.

A typical lens system includes many lens elements. Aberrations in a lens system can change over time due to the aging of the lens system materials, environmental effects, or the non-linearity of control algorithms used to adjust the lens system. For example, each lens has a heating curve associated with it, such that as the lens heats up due to environmental conditions or due to lens use during exposures, the effective focus length of the lens changes. Air pressure also has a predictable effect on the lens elements and their focus values. Aberrations in the lens system can also change due to maintenance events or other mechanical effects, such as shipping. Control algorithms in the exposure tools are typically used to adjust one or more of the lens elements to compensate for measured external effects or internal effects.

CD control and image integrity of device layers is a direct function of several components, including dose and focus of the exposure tool. Typically, dose feedback is an active run to run control parameter. Focus feedback, however, typically has not been an active run to run control parameter. Typically, the optimal focus setting for any given product/tool/layer/reticle context value combination is determined at the context inception and used throughout the life of the product. In the event that an intrusive tool event occurs and the tool baseline focus is lost or changed, the process set point for each context value is reestablished. Typical ex-situ tool focus monitoring techniques have not exhibited the accuracy and precision to substantiate product process set point changes based on measured focus values. These techniques have typically been used only for monitoring by providing flags for obvious large focus excursions.

Focus is typically controlled through explicit context value control. The best focus process point is typically determined by evaluating focus exposure process windows at the time of the new context introduction. This best focus process value is then used for the lifetime of the context value. A disadvantage of this process is that there is no process available to reset the focus values in the presence of tool baseline focus shifts or to correct for uncompensated focus drifts in the exposure tool. In the event of a large change in the tool focus, there is no direct method to apply the new setting to the context data.

Exposure tool focus offsets induced on product as a result of in-situ focus sensor systems inability to measure edge of substrate image fields and large focus rate of change of topographical features can result in significant process and device yield loss due to poor focus plane determination and fitting. Typically, exposure tools have significant problems determining focal image planes on edge die or over sever topography. Typical exposure tools require some fitting functions from neighboring fields or a partial system shutdown to prevent erroneous data from being used in the fitting functions.

Dark field microscopy and inspection are fundamental arts of inspection in many industries. There are several components of the inspection tool hardware that contribute to the illumination of the sample in darkfield inspection, such as the illumination source itself, the beam delivery hardware, the darkfield splitter hardware, the lens objective design, and the camera adapter. Each of these components plays a significant role in the illumination of the sample and the collection of the darkfield image formed from the sample. Typical methods provide for illumination uniformity measurements along the Cartesian x and y axis. This is insufficient. Illumination uniformity measurements along the Cartesian x and y axis do not allow the investigation of the entire circumference of the system pupils in azimuthal increments.

SUMMARY

One embodiment of the present invention provides an inspection system. The inspection system comprises an illumination source configured to illuminate a blazed phase grating sample, image collection pathways and an imaging system configured to capture an image of a sample point of the blazed phase grating sample, and a controller configured to adjust the illumination source in response to an analysis of the image of the sample point to determine illumination uniformity of the inspection system.

BRIEF DESCRIPTION OF THE DRAWINGS

Embodiments of the invention are better understood with reference to the following drawings. The elements of the drawings are not necessarily to scale relative to each other. Like reference numerals designate corresponding similar parts.

FIGS. 9A-9P are images illustrating embodiments of portions of a BPG sample generated by an exposure tool using a reticle including the array of blazed phase gratings.

FIG. 10 is a diagram illustrating one embodiment of an exposure field layout for generating a BPG sample in an exposure tool.

FIG. 11A is a diagram illustrating one embodiment of an exposure field.

FIG. 11B is a diagram illustrating one embodiment of sampling regions for an exposure field.

DETAILED DESCRIPTION

Figure 1:
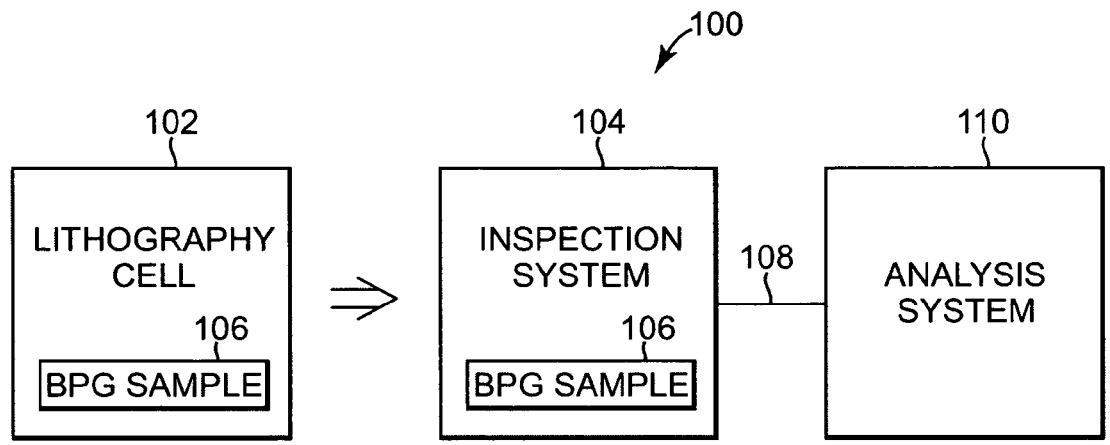
FIG. 1 is a block diagram illustrating one embodiment of an optical lithography and inspection system.

FIG. 1 is a block diagram illustrating one embodiment of an optical lithography and inspection system 100. Optical lithography and inspection system 100 includes a lithography cell 102, an inspection system 104, and an analysis system 110. Inspection system 104 is communicatively coupled to analysis system 110 through communication link 108. Lithography cell 102 includes an exposure tool, resist coating tool, development processing tool, and/or other suitable tools used for performing optical lithography on semiconductor wafers. Inspection system 104 comprises a microscope or other suitable inspection tool for inspecting semiconductor wafers. Analysis system 110 receives inspection data for an inspected semiconductor wafer from inspection system 104 and analyzes the inspection data. In one embodiment, analysis system 110 is part of inspection system 104.

In one embodiment, optical lithography and inspection system 100 is configured to generate, inspect, and analyze Blazed Phase Grating (BPG) samples 106 for obtaining parameters of an exposure tool of lithography cell 102 and/or for obtaining parameters of inspection system 104. In one embodiment of the invention, a BPG sample 106 is periodically generated by an exposure tool in lithography cell 102. The BPG sample 106 is generated in the exposure tool using a reticle including blazed phase gratings for generating asymmetric spectra that allows radial and azimuthal sampling of the pupil of the exposure tool, as described in more detail later in this Detailed Description. The radial sampling is achieved by varying the pitch or grating periods of the blazed phase gratings and the azimuthal sampling is achieved by providing different angular orientations of the blazed phase gratings on the reticle. The reticle, including the blazed phase gratings configured for radial and azimuthal sampling of the pupil of the exposure tool, is exposed at several focus steps. After exposure, the BPG sample 106 includes a plurality of asymmetric relief gratings formed in photoresist that correlate to exposure tool parameters.

The BPG sample 106 is passed to inspection system 104 for collecting images. Inspection system 104 obtains images of BPG sample 106 at a plurality of sample points. Each image of each sample point includes relief gratings of BPG sample 106 generated by each of the angular orientations of the blazed phase gratings of the reticle at each of the focus steps. The images are passed to analysis system 110. Analysis system 110 analyzes the images to determine parameters of the exposure tool of lithography cell 102 and/or to determine parameters of inspection system 104. For the exposure tool, analysis system 110 can determine the scan direction parameters, the field attribute parameters, such as focus, Isofocal Deviation (IFD), tilt about x or x tilt (RX), and tilt about y or y tilt (RY), range, and/or the lens system aberrations, such as tilt, coma, astigmatism, spherical, three fold, four fold, and five fold aberrations. For inspection system 104, analysis system 110 can determine illumination parameters.

Figure 2:
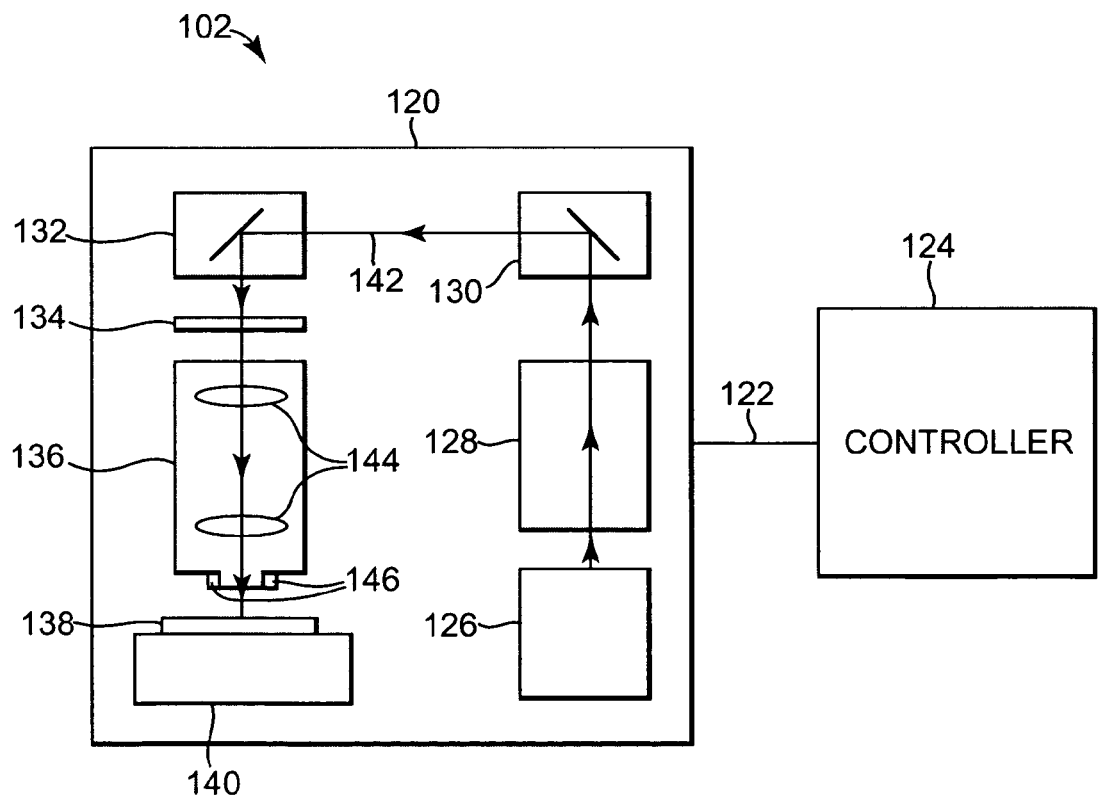
FIG. 2 is a diagram illustrating one embodiment of an exposure tool of an optical lithography cell.

FIG. 2 is a diagram illustrating one embodiment of an exposure tool 120 of lithography cell 102. Lithography cell 102 includes exposure tool 120 and controller 124. Exposure tool 120 is communicatively coupled to controller 124 through communication link 122. In one embodiment, exposure tool 120 includes an illumination source 126, an illumination source lens system 128, a first mirror 130, a second mirror 132, a reticle 134, a lens system 136, focus sensors 146, and a stage 140. In other embodiments, exposure tool 120 includes other components. A sample 138 is placed on stage 140 for exposure. In one embodiment, exposure tool 120 is used to generate BPG sample 106.

In one embodiment of the invention, exposure tool 120 is a stepper exposure tool in which exposure tool 120 exposes a small portion of sample 138 at one time and then steps sample 138 to a new location to repeat the exposure. In another embodiment of the invention, exposure tool 120 is a scanner in which reticle 134 and sample 138 are scanned passed the field of lens system 136 that projects the image of reticle 134 onto sample 138. In another embodiment, exposure tool 120 is a step and scan exposure tool, which combines both the scanning motion of a scanner and the stepping motion of a stepper. Regardless of the method used, exposure tool 120 exposes sample 138.

In one embodiment, illumination source 126 includes a 193 nm wavelength Argon Fluoride (ArF) excimer laser, a 248 nm wavelength Krypton Fluoride (KrF) excimer laser, or other suitable light source. Illumination source 126 provides light to illumination source lens system 128 on optical path 142. Illumination source lens system 128 filters, conditions, and aligns the light from illumination source 126 to provide the light to first mirror 130 on optical path 142. First mirror 130 reflects the light on optical path 142 to second mirror 132. Second mirror 132 reflects the light on optical path 142 to reticle 134. In one embodiment, first mirror 130 and second mirror 132 include other optics for further conditioning or aligning the light on optical path 142.

Reticle 134 includes an image for projecting onto sample 138 on stage 140. Reticle 134 is a glass or quartz plate containing information encoded as a variation in transmittance and/or phase about the features to be printed on sample 138. In one embodiment, reticle 134 is a BPG reticle for generating asymmetric relief gratings on sample 138 for evaluating exposure tool 120. Lens system 136 focuses the light on optical path 142 from reticle 134 onto sample 138 for writing on sample 138. In one embodiment, lens system 136 includes a plurality of lens elements 144 that can be adjusted to correct for focus, lens aberrations, and other parameters for maintaining critical dimension (CD) uniformity. Focus sensors 146 adjust the focal plane during the exposure of sample 138 to maintain the focus in response to changes in topography of sample 138.

Stage 140 holds sample 138 for exposure. Stage 140 and/or reticle 134 are positioned relative to lens system 136 for exposing portions of sample 138 depending on whether exposure tool 120 is a stepper, scanner, or step and scan exposure tool. Controller 124 controls the operation of exposure tool 120. In one embodiment, controller 124 controls the position of and/or adjusts illumination source 126, illumination source lens system 128, first mirror 130, second mirror 132, reticle 134, lens system 136, and stage 140 for exposing sample 138. In one embodiment, controller 124 controls exposure tool 120 to expose sample 138 using a BPG reticle for reticle 134 to generate a BPG sample 106 for evaluating exposure tool 120.

In one embodiment, focus sensors 146 are used to obtain relief measurements of BPG sample 106 in place of the images of BPG sample 106 obtained by inspection system 104. In this embodiment, the reflected intensity of BPG sample 106 is determined as a function of the sample process parameters. The reflected intensity data provides data similar to the data obtained from images of BPG sample 106. The reflected intensity data is analyzed in a similar manner as the image data to determine parameters of exposure tool 120.

Figure 3:
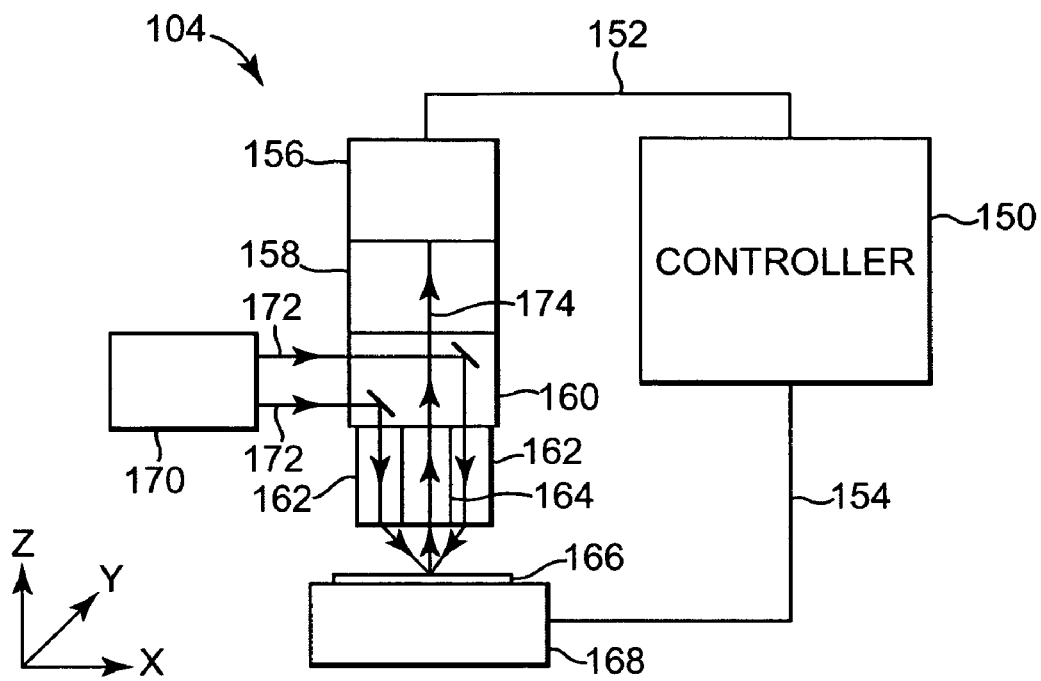
FIG. 3 is a diagram illustrating one embodiment of an inspection system.

FIG. 3 is a diagram illustrating one embodiment of inspection system 104. In one embodiment, inspection system 104 is a microscope or other suitable inspection tool. Inspection system 104 includes a controller 150, imaging system 156, lens system 158, illumination source 170, illumination beam steering components 160 and 162, objective 164, and stage 168. In one embodiment, controller 150 is electrically coupled to imaging system 156, lens system 158, beam steering components 160 and 162, and objective 164 through communication link 152 and to stage 168 through communication link 154. A sample 166 to be inspected is placed on stage 168. In one embodiment, sample 166 is BPG sample 106.

In one embodiment, imaging system 156 includes a Charge-Coupled Device (CCD) camera, a complementary metal-oxide-semiconductor (CMOS) imaging device, or other suitable device capable of obtaining images of sample 166. In one embodiment of the invention, imaging system 156 obtains data from color images, such as RGB, YIQ, HSV, or YCbCr, of sample 166. In another embodiment of the invention, imaging system 156 obtains data from grayscale images of sample 166. In one embodiment, the images are 480×640 pixels or other suitable resolution. The images are saved in JPEG, TIF, bitmap, or other suitable file format. Lens system 158 focuses images of sample 166 for recording by imaging system 156.

Objective 164 magnifies the portion of sample 166 under inspection. Illumination source 170 provides light along optical path 172 to illuminate sample 166. In one embodiment, illumination source 170 provides Deep Ultraviolet (DUV) light to illuminate sample 166. A DUV illumination source provides for optimizing the inspection system 104 illumination wavelength for increased BPG sample 106 measurement sensitivity and accuracy. The inspection system 104 illumination wavelength can also be optimized to match the optical parameters of the BPG photoresist or surface materials.

Illumination beam steering components 160 and 162 steer the light from illumination source 170 to sample 166 in either a darkfield inspection mode or a brightfield inspection mode. In the darkfield inspection mode, light for illuminating sample 166 strikes sample 166 at an angle such that only light reflected or diffracted by features of sample 166 enters objective 164. In the illustrated embodiment, illumination beam steering components 160 and 162 are steering light in a darkfield inspection mode, as indicated by optical path 172. Light reflected from sample 166, as indicated by optical path 174, is collected by objective 164, lens system 158, and imaging system 156 to obtain images of sample 166. In another embodiment, inspection system 104 is configured in a brightfield inspection mode. In one embodiment, in the brightfield inspection mode, sample 166 is illuminated from directly above by steering light from illumination source 170 through the center of objective 164 using a beam splitter of illumination beam steering component 160. In other embodiments, illumination beam steering components 160 and 162 include any number of suitable components for steering light from illumination source 170 to sample 166 in either a darkfield inspection mode or a brightfield inspection mode, such as mirrors, prisms, beam splitters, etc.

Stage 168 positions sample 166 relative to objective 164 for obtaining images of portions of sample 166. In one embodiment, stage 168 is moved relative to objective 164 in the horizontal x and y directions to select portions of sample 166 for inspection and in the vertical z direction to adjust the focus of inspection system 104. In other embodiments, objective 164, illumination beam steering components 160 and 162, lens system 158, and/or imaging system 156, are positioned relative to sample 166 to select portions of sample 166 for inspection and to adjust the focus of inspection system 104.

Controller 150 controls the operation of inspection system 104. Controller 150 controls the position of stage 168 relative to objective 164 and the position or adjustment of illumination beam steering components 160 and 162, lens system 158, and imaging device 156. Controller 150 receives images of sample 166 from imaging device 156 though communication link 152. In one embodiment, controller 150 analyzes the images and outputs the analysis results. In another embodiment, controller 150 passes the images to analysis system 110, which performs the analysis and outputs the analysis results.

Inspection system 104 is configured to collect a plurality of images of sample 166 at predefined locations. In one embodiment, inspection system 104 collects images of BPG sample 106 at a plurality of sample points for analyzing the images to determine parameters of exposure tool 120 and/or inspection system 104. A file in a suitable file format is used to describe the locations of sample points of BPG sample 106. Controller 150 uses the file to drive inspection system 104 to the sample point locations and collect an image of each sample point location. The sample point locations of BPG sample 106 are defined relative to each other and/or relative to an absolute location on BPG sample 106. In one embodiment, the file contains a relatively small sample set, such as 88 sample point locations per exposure field. In other embodiments, the file contains a large number of sample point locations, such as hundreds of sample point locations per exposure field or thousands of sample point locations per wafer.

Inspection system 104 obtains an image of BPG sample 106 at each predefined-sample point location. In one embodiment, each image is assigned a unique name including a sequentially incremented variable string. Each image, which is identified by the unique variable string, is associated to the particular predefined sample point location on BPG sample 106. Inspection system 104 obtains the images at the predefined sample point locations in sequential order or in any other suitable sequence as long as the unique name assigned to each image is linked to or associated with the predefined sample point location on BPG sample 106.

In another embodiment, inspection system 104 is an Atomic Force Microscope (AFM), scatterometer, or other suitable profilometer for obtaining physical relief measurements of BPG sample 106 in place of images of BPG sample 106. In this embodiment, the surface profile of BPG sample 106 is determined as a function of position. The surface profile data provides data similar to the data obtained from images of BPG sample 106. The surface profile data is analyzed in a similar manner as the image data to determine parameters of exposure tool 120.

Figure 4:
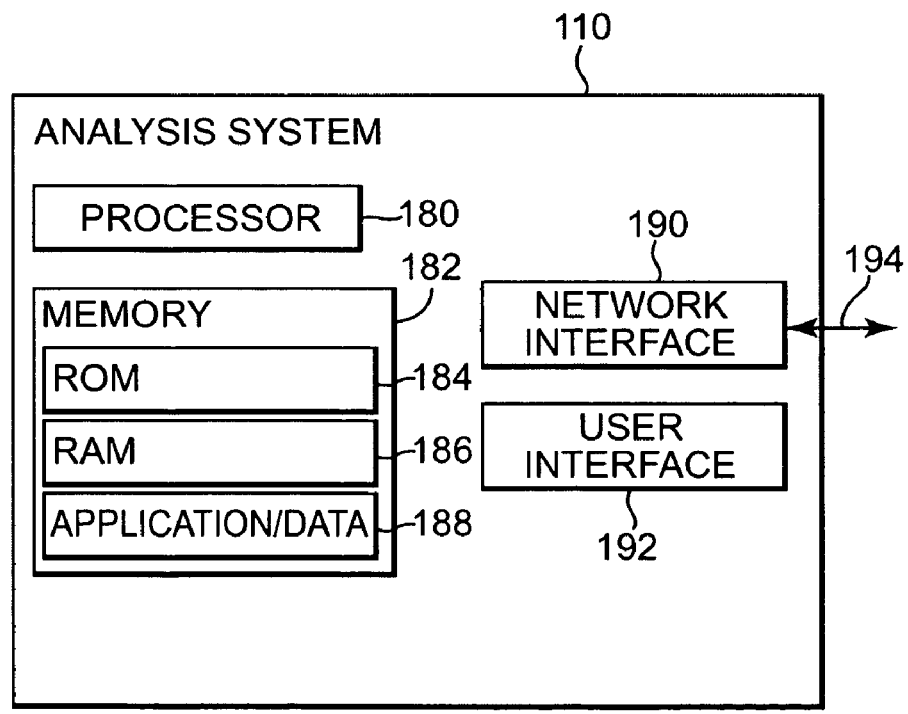
FIG. 4 is a block diagram illustrating one embodiment of an analysis system for analyzing images of Blazed Phase Grating (BPG) samples.

FIG. 4 is a block diagram illustrating one embodiment of analysis system 110 for analyzing images of sample points of BPG sample 106. In one embodiment, analysis system 110 includes a processor 180, a memory 182, a network interface 190, and a user interface 192. In one embodiment, memory 182 includes a Read Only Memory (ROM) 184, a Random Access Memory (RAM) 186, and an application/data memory 188. Network interface 190 is communicatively coupled to a network through communication link 194.

Analysis system 110 executes an application program for analyzing images of sample points of BPG sample 106 obtained by inspection system 104. The images of sample points of BPG sample 106 are stored in application/data memory 188 or any other computer readable medium. In addition, the application program is loaded from application/data memory 188 or any other computer readable medium. Processor 180 executes commands and instructions for analyzing the images of sample points of BPG sample 106 from inspection system 104. In one embodiment, ROM 184 stores the operating system for analysis system 110 and RAM 186 temporarily stores the images of sample points of BPG sample 106 being analyzed and other application data and instructions for analyzing the images.

Network interface 190 communicates with a network for passing data between analysis system 110 and other systems. In one embodiment of the invention, network interface 190 includes communication link 108 for communicating with inspection system 104. In one embodiment, network interface 190 communicates using a SECS/GEM protocol, a machine manager protocol, a process job manager protocol, or other suitable machine messaging protocol. User interface 192 provides an interface to analysis system 110 for users to configure, operate, and review and/or output results from analysis system 110. In one embodiment, user interface 192 includes a keyboard, a monitor, a mouse, and/or any other suitable input or output device.

Memory 182 can include main memory, such as RAM 186, or other dynamic storage device. Memory 182 can also include a static storage device for application/data memory 188, such as a magnetic disk or optical disk. Memory 182 stores information and instructions to be executed by processor 180. In addition, memory 182 stores images of sample points of BPG sample 106 from inspection system 104 and other data, such as results, for analysis system 110. One or more processors in a multi-processor arrangement can also be employed to execute a sequence of instructions contained in memory 182. In other embodiments, hardwired circuitry can be used in place of or in combination with software instructions to implement analysis system 110. Thus, embodiments of analysis system 110 are not limited to any specific combination of hardware circuitry and software.

The term "computer readable medium," as used herein, refers to any medium that participates in providing instructions to processor 180 for execution or data to processor 180. Such a medium can take many forms, including for example, non-volatile media, volatile media, and transmission media. Non-volatile media include, for example, optical or magnetic disks. Volatile media includes dynamic memory. Transition media include coaxial cables, copper wire, and fiber optics. Transmission media can also take the form of acoustic or light waves, such as those generated during radio frequency (RF) and infrared (IR) data communications. Common forms of computer readable media include, for example, a floppy disk, a flexible disk, a hard disk, magnetic tape, any other magnetic mediums, a CD-ROM, DVD, any other optical medium, a RAM, a programmable read-only memory (PROM), an electrical programmable read-only memory (EPROM), an electrically erasable programmable read-only memory (EEPROM), any other memory chip or cartridge, or any other medium from which a computer can read.

In one embodiment, the analysis of the images of sample points of BPG sample 106 by analysis system 110 is initiated automatically once the images are obtained by inspection system 104 or manually by a user. The results are automatically reported or stored for later review by a user. The analysis of the images of sample points of BPG sample 106 performed by analysis system 110 is described in greater detail later in this Detailed Description.

Figure 5A:
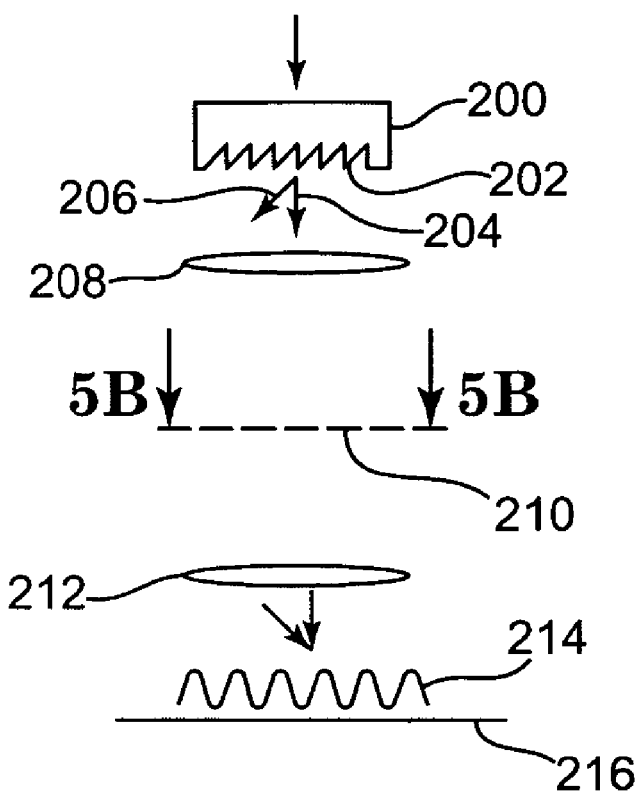
FIG. 5A is a schematic diagram illustrating one embodiment of generating a BPG sample using an ideal BPG reticle.
Figure 5B:
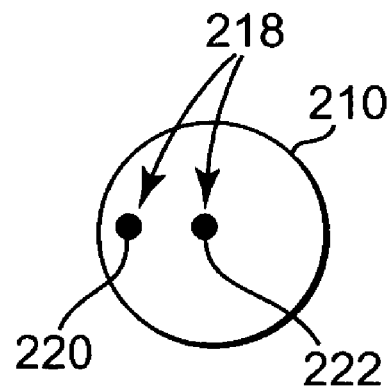
FIG. 5B is a cross-sectional view of an illumination image taken with the ideal BPG reticle illustrated in FIG. 5A.

FIG. 5A is a schematic diagram illustrating one embodiment of generating a BPG sample using an ideal BPG reticle. FIG. 5B is a cross-sectional view of an illumination image taken with the ideal BPG reticle illustrated in FIG. 5A. BPG reticle 200 has an ideal blazed phase grating 202. A blazed phase grating transmits diffracted light preferentially in one direction. A simple grating transmits diffracted light in the same way on either side of the zeroth order with light incident normal to the grating surface. An ideal blazed phase grating 200 transmits diffracted light into two portions 204 and 206. The two portions are focused by a lens or lens system 208 onto a pupil plane 210 to produce an illumination pattern 218 (see FIG. 5B). In one embodiment, lens 208 is a convex lens or other suitable lens or lens system.

In the ideal case, illumination pattern 218 includes a two-peak illumination image indicated by peaks 220 and 222. Image pattern 218 is focused by a lens or lens system 212 and printed on a surface of high absorption photoresist 214 on the surface of a wafer 216. In one embodiment, lens 212 is a convex lens or other suitable lens or lens system. An ideal blazed phase grating provides an image with a sinusoidal relief in the high absorption photoresist 214. The relief depth varies as a function of the focus due to the interference effects or degree of phase matching between the zeroth order diffraction and the first order diffraction. The relief depth increases as the phase difference between the zeroth order diffraction and the first order diffraction decreases, thereby producing the deepest relief image at the best focus. The diffraction efficiency of the image can be recorded as a digitized darkfield image by inspection system 104 and processed by analysis system 110 to determine aberrations of the lens or lens system 208 and 212. By varying the angular orientations of the diffraction grating, relief images are formed in photoresist 214 by illuminating different azimuths of pupil plane 210. The aberrations are determined by analyzing the variation of focus with respect to the azimuthal orientation of the grating.

Figure 6A:
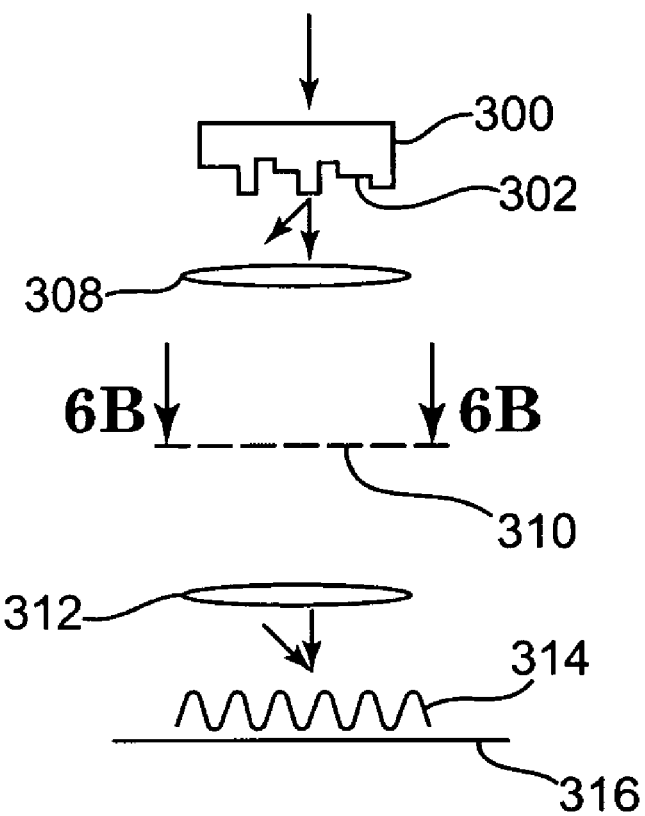
FIG. 6A is a schematic diagram illustrating one embodiment of generating a BPG sample using a relatively easily manufactured BPG reticle.
Figure 6B:
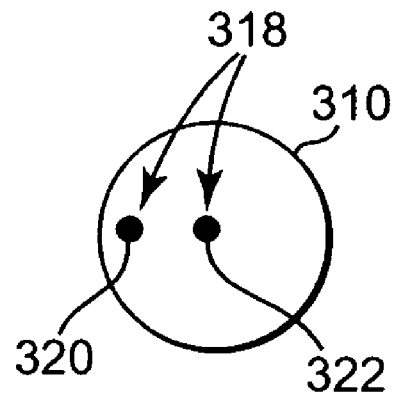
FIG. 6B is a cross-sectional view of an illumination image taken with the relatively easily manufactured BPG reticle illustrated in FIG. 6A.

FIG. 6A is a schematic diagram illustrating one embodiment of generating a BPG sample using a relatively easily manufactured blazed phase grating reticle as compared to ideal BPG reticle 200. FIG. 6B is a cross-sectional view of an illumination image taken with the relatively easily manufactured blazed phase grating reticle illustrated in FIG. 6A. The grating profile of blazed phase grating reticle 300 provides a two-beam illumination of an image using a reticle that is easier to manufacture than ideal blazed phase grating reticle 200. Reticle 300 includes a profile 302, which separates light passing through reticle 300. In one embodiment, reticle 300 is made from the same material used for printing integrated circuit patterns (e.g., quartz or any other transparent material). In one embodiment, reticle 300 is about 0.25 inches thick and relief steps are appropriately sized to give the phase step desired. Any light wavelength can be used for the exposure, such as 248 nm, 193 nm, and 157 nm.

Lens or lens system 308 focuses an image on pupil plane 310 (FIG. 6B) as illumination pattern 318. A two-beam illumination image is provided, where image 320 is a first order diffraction and image 322 is the zeroth order diffraction. Light is focused by lens or lens system 312 to provide an image-with a sinusoidal relief in the high absorption photoresist 314 on the surface of a wafer 316. The relief depth varies as a function of the focus due to the interference effects or degree of phase matching between the zeroth order diffraction and the first order diffraction. The relief depth increases as the phase difference between the zeroth order diffraction and the first order diffraction decreases, thereby producing the deepest relief image at the best focus. In one embodiment, the entire sinusoidal relief is captured in the upper most layer of the photoresist 314 so as not to introduce bulk material or substrate optical effects during the inspection process.

Profile 302 of reticle 300 provides a two-beam illumination without using ideal profile 202 (FIG. 5A). In one embodiment, profile 302 includes three phase regions and each phase region provides light 90 degrees out of phase relative to an adjacent region. In one embodiment, a first region provides a zero degree phase shift for light exiting relative to the light entering reticle 300, a second region provides 90 degree phase shifted light, and a third region provides 180 degree phase shifted light. In one embodiment, the second region is twice as wide as the first and third regions. In another embodiment, profile 302 includes three regions having equal widths, where the first region is opaque to block the transmission of light, the second region is transparent to provide a zero degree phase shift for light exiting relative to the light entering reticle 300, and the third region is also transparent and provides 60 degree phase shifted light. In other embodiments, other configurations are used based on the accuracy or sensitivity desired for evaluating lens or lens system 308 and 312, and based on the wavelength of light used for the exposure.

Similar to the ideal case described above with reference to FIGS. 5A-5B, the diffraction efficiency of the image formed in the photoresist in this case can be recorded as a digitized darkfield image by inspection system 104 and processed by analysis system 110 to determine aberrations of the lens or lens system 308 and 312. By varying the angular orientations of the diffraction grating, relief images are formed in photoresist 314 by illuminating different azimuths of pupil plane 310. The aberrations are determined by analyzing the variation of focus with respect to the azimuthal orientation of the grating.

One blazed phase grating profile 302 suitable for implementing the current invention is disclosed in U.S. Pat. No. 6,606,151 entitled "Grating Patterns and Method for Determination of Azimuthal and Radial Aberration," which is hereby incorporated herein by reference.

Figure 7:
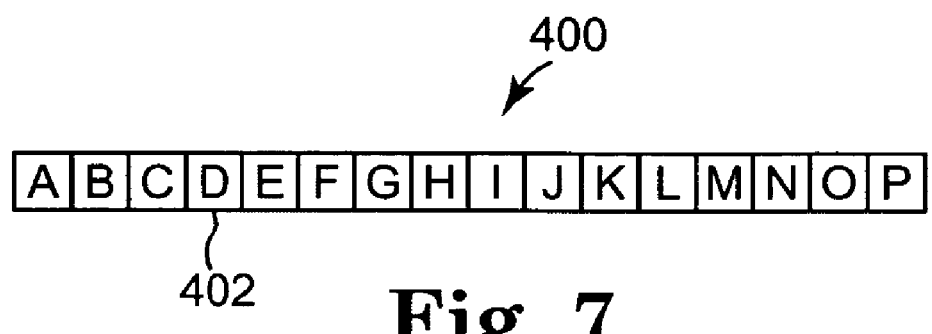
FIG. 7 is a diagram illustrating one embodiment of an array of blazed phase gratings.

FIG. 7 is a diagram illustrating one embodiment of an array of blazed phase gratings 400. In one embodiment, array of blazed phase gratings 400 includes 16 components labeled A-P, such as component D 402. Each array 400 component A-P includes a blazed phase grating, such as grating 302, oriented at a different angle for sampling a different portion of a pupil of a lens system. In one embodiment, each array 400 component A-P is oriented 22.5 degrees with respect to an adjacent component A-P. For example, component A may be oriented at zero degrees, component B at 22.5 degrees, component C at 45 degrees, component D at 67.5 degrees, etc., and component P at 337.5 degrees. In other embodiments, the number of array 400 components and the angular orientations of the components can vary based on the number of pupil portions to be sampled.

When exposed in an exposure tool, such as exposure tool 120, each component A-P of array 400 generates a sinusoidal relief image in the photoresist at the angular orientation of the component A-P as described above with reference to FIGS. 5A-6B. Each component A-P of array 400 generates a relief image in the photoresist by illuminating a different azimuth of the pupil of the exposure tool based on the angular orientation.

The radial dependence of a lens or lens system can be determined by evaluating the lens or lens system using different pitches or grating periods for components A-P of array of blazed phase gratings 400. The location of the first order beam depends on the grating period as follows:

$$x = \frac{\lambda}{\text{pitch} * NA}$$

Where:
x=the position of the first order beam in units of NA;
λ=the wavelength of light; and
NA=the numerical aperture of the lens system.

By varying the grating period, information about the radial components of the aberrations can be obtained and evaluated for a particular lens or lens system. A larger grating period causes light to be diffracted by a smaller angle and therefore illuminates the pupil closer to the zero order, undiffracted beam. A smaller grating period causes light to be diffracted by a larger angle and therefore illuminates the pupil farther from the zero order, undiffracted beam. By using a reticle including more than one array 400 of components A-P with different grating periods, several different radii of the lens or lens system can be sampled. The radial dependence of the aberrations can then be determined.

The pitch or grating period of components A-P of array 400 is selected to illuminate a selected radius of the pupil of the exposure tool to generate the relief images. Therefore, by varying the angular orientation of components A-P and by setting the pitch or grating period of components A-P, the exposure tool generates the relief images by illuminating the corresponding azimuthal and radial portion of the pupil of the exposure tool.

A BPG reticle including any suitable number of arrays 400 of components A-P is used to generate a BPG sample 106. The BPG reticle can include any number of blazed phase grating arrays 400 having different pitches or grating periods. In one embodiment, a BPG reticle including at least four arrays 400 of components A-P with different pitches or grating periods is used to generate BPG sample 106 in exposure tool 120.

Figure 8:
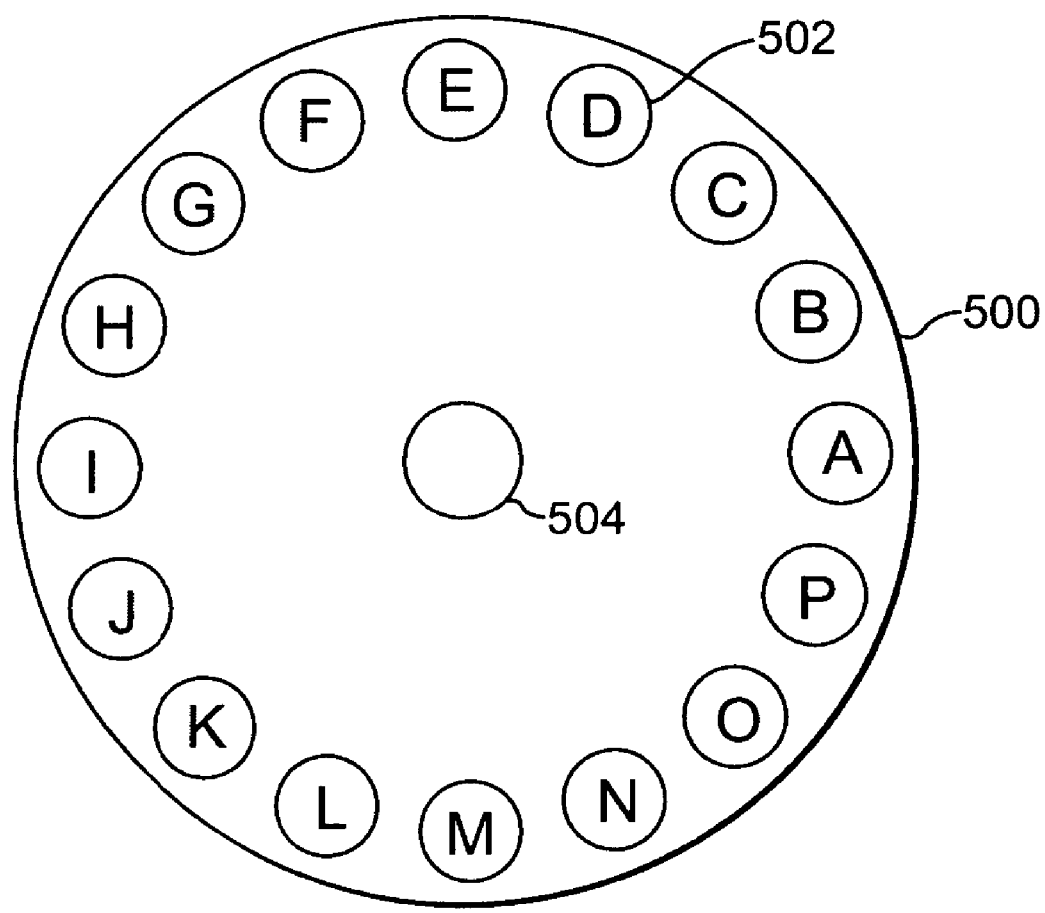
FIG. 8 is a diagram illustrating one embodiment of a pupil of a lens system.

FIG. 8 is a diagram illustrating one embodiment of a pupil 500 of a lens system, such as lens system 136 of exposure tool 120 or objective 164 of inspection system 104. Pupil 500 includes portions A-P, such as portion D 502, and portion 504. Portion 504 corresponds to the zeroth order diffraction. Each portion A-P of pupil 500 corresponds to the first order diffraction and the angular orientation of grating components A-P of array 400. For example, component D 402 of blazed phase grating array 400 corresponds to portion D 502 of pupil 500. In some embodiments, higher order diffractions may be included in pupil 500 but the higher order diffractions have a negligible effect on the aberration analysis. The size (circumference) of portions A-P vary based on the sigma setting for exposure tool 120. The placement of portion 504 and portions A-P with respect to the center of pupil 500 and/or with respect to each other varies based on the illumination settings for exposure tool 120.

By increasing the pitch or grating period of component D 402 of blazed phase grating array 400, the portion D 502 of pupil 500 moves closer to the center of pupil 500 and decreases the radius of the azimuth sampled. By decreasing the pitch or grating period of component D 402 of blazed phase grating array 400, the portion D 502 of pupil 500 moves farther away from the center of pupil 500 and increases the radius of the azimuth sampled.

FIGS. 9A-9P are images 600-630 illustrating embodiments of portions of BPG sample 106 generated by exposure tool 120 using a reticle including an array of blazed phase gratings 400. Images 600-630 illustrate portions of BPG sample 106 exposed through components A-P of array 400 and portions A-P of pupil 500, respectively. Portions of BPG sample 106 exposed with an accurate focus at the plane of the photoresist layer or at the surface of the photoresist layer develop a greater amount of relief or difference in the surface height of the developed photoresist than in portions where lens system 136 aberrations are present and the image is defocused to a greater or lesser degree. The degree of the relief gratings resulting at respective exposure locations is a function of the aberrations present in lens system 136. Parameters for exposure tool 120 can be extracted based on the degree of the relief gratings in the developed photoresist using inspection system 104 and analysis system 110.

In one embodiment, BPG sample 106 is prepared to improve the data integrity by reducing or removing optical noise. In one embodiment, BPG sample 106 is prepared by applying an optically opaque mask layer on the wafer before applying the photoresist layer. The optically opaque mask layer blocks reflections from reflective product features so that the product features do not interfere with the BPG sample 106 image data. In another embodiment, a thin metal coating or other suitable reflective coating is applied on top of the processed BPG sample 106 to block reflections from underlying reflective product features during the inspection of BPG sample 106 relief gratings. In another embodiment, a protective top coat layer is applied on the BPG photoresist layer to prevent contamination of the photoresist due to wet or dry environmental conditions during the exposure of the BPG photoresist.

FIG. 10 is a diagram illustrating one embodiment of an exposure field layout 700 for generating BPG sample 106 in exposure tool 120. Exposure field layout 700 includes seven exposure fields 702A-702G oriented for BPG sample 106 as indicated by wafer orientation indicator 706. In other embodiments, a different number of exposure fields can be used. The exposure fields can also be laid out on the wafer in any suitable manner. In one embodiment, an exposure field layout that completely covers an entire BPG sample 106 with relief images is used.

The arrows in each exposure field, such as arrow 704 in exposure field 702A, indicate the scan direction for each exposure field 702A-702G. The scan direction for each exposure field 702A-702G varies based on the desired parameters to be extracted from the exposure field 702A-702G of BPG sample 106. The scan direction can be up, down, or both up and down within a single exposure field.

Controller 124 uses exposure field layout 700 to control exposure tool 120 to generate BPG sample 106 based on exposure field layout 700. BPG sample 106 is generated based on exposure field layout 700 using a BPG reticle including at least one array of blazed phase gratings 400. In one embodiment, the BPG reticle includes a plurality of blazed phase grating arrays 400 each having a different grating pitch. Exposure tool 120 exposes BPG sample 106 with array of blazed phase gratings 400 at any suitable number of focus steps. In one embodiment, exposure tool 120 exposes BPG sample 106 at 17 different focus steps. In one embodiment of the invention, the focus steps are in increments of 50 nm for an exposure tool 120 using an illumination source 126 having a wavelength of 193 nm. In other embodiments, other suitable focus steps are used, such that the focus steps cover a range greater than the expected focus change due to lens system 136 aberrations to be measured. For example, the focus steps could be set to one third of the wavelength of illumination source 126 divided by the square of the numerical aperture of lens system 136.

In one embodiment, the scan direction of exposure tool 120 varies between focus steps within an exposure field 702A-702G when exposing BPG sample 106 with blazed phase grating array 400. Therefore, every other exposure of BPG sample 106 with blazed phase grating array 400 is scanned in the opposite direction.

FIG. 11A is a diagram illustrating one embodiment of an exposure field 702. Exposure field 702 includes a length 708 and a width 710. The orientation of exposure field 702 is indicated by wafer orientation indicator 706. In one embodiment, exposure field 702 has a width 710 of 26 mm and a length 708 of 32 mm. In other embodiments, other length 708 and width 710 dimensions can be used. In one embodiment of the invention, the width 710 is across a slit of exposure tool 120 and the length 708 is across the scan of exposure tool 120. In other embodiments, exposure field 702 is oriented for exposure by exposure tool 120 in another suitable manner.

FIG. 11B is a diagram illustrating one embodiment of sampling regions for an exposure field 702. The orientation of exposure field 702 is indicated by wafer orientation indicator 706. Exposure field 702 is divided into 88 portions, wherein an image of a sample point is obtained in each portion 1-88. In one embodiment, eight images are obtained across the width 710 of exposure field 702, which samples the slit of exposure tool 120, and eleven images are obtained across the length 708 of exposure field 702, which samples the scan of exposure tool 120, for a total of 88 images per exposure field 702. In other embodiments, images of any suitable number of sample points per exposure field 702 may be obtained based on the desired parameters to be determined from the images.

Figure 12:
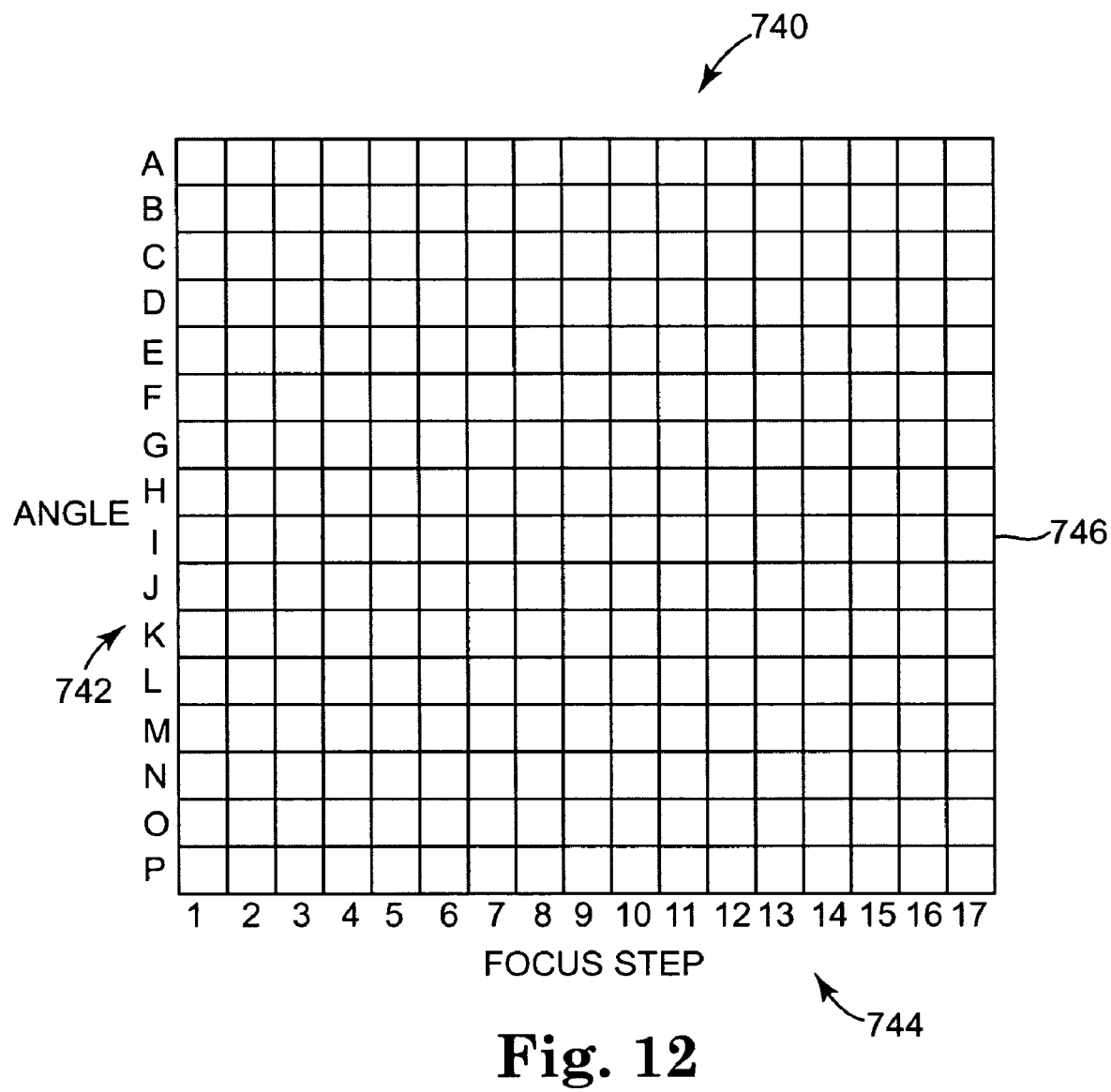
FIG. 12 is a diagram illustrating one embodiment of an image layout for a sample point generated using an array of blazed phase gratings.

FIG. 12 is a diagram illustrating one embodiment of an image layout for a sample point 740 generated using an array of blazed phase gratings 400. Sample point 740 of BPG sample 106 is generated by exposure tool 120 by exposing BPG sample 106 with array of blazed phase gratings 400 at a number of different focus steps as previously described. Components A-P of blazed phase grating array 400 are scanned by exposure tool 120 at each of 17 focus steps to produce a two-dimensional array of relief images on the surface of BPG sample 106 for each sample point 740 of BPG sample 106. Each relief image varies in exposure by the angular orientation of lens system 136 illumination in one direction, as indicated at 742, and by focus in the other direction, as indicated at 744. Each relief image corresponds to exposure by one component A-P of blazed phase grating array 400 at a different focus step. For example, relief image 746 is generated by component I of blazed phase grating array 400 at focus step 17. Inspection system 104 obtains the images of multiple sample points 740 for analyzing the images to determine parameters of exposure tool 120 and/or inspection system 104.

Figure 13:
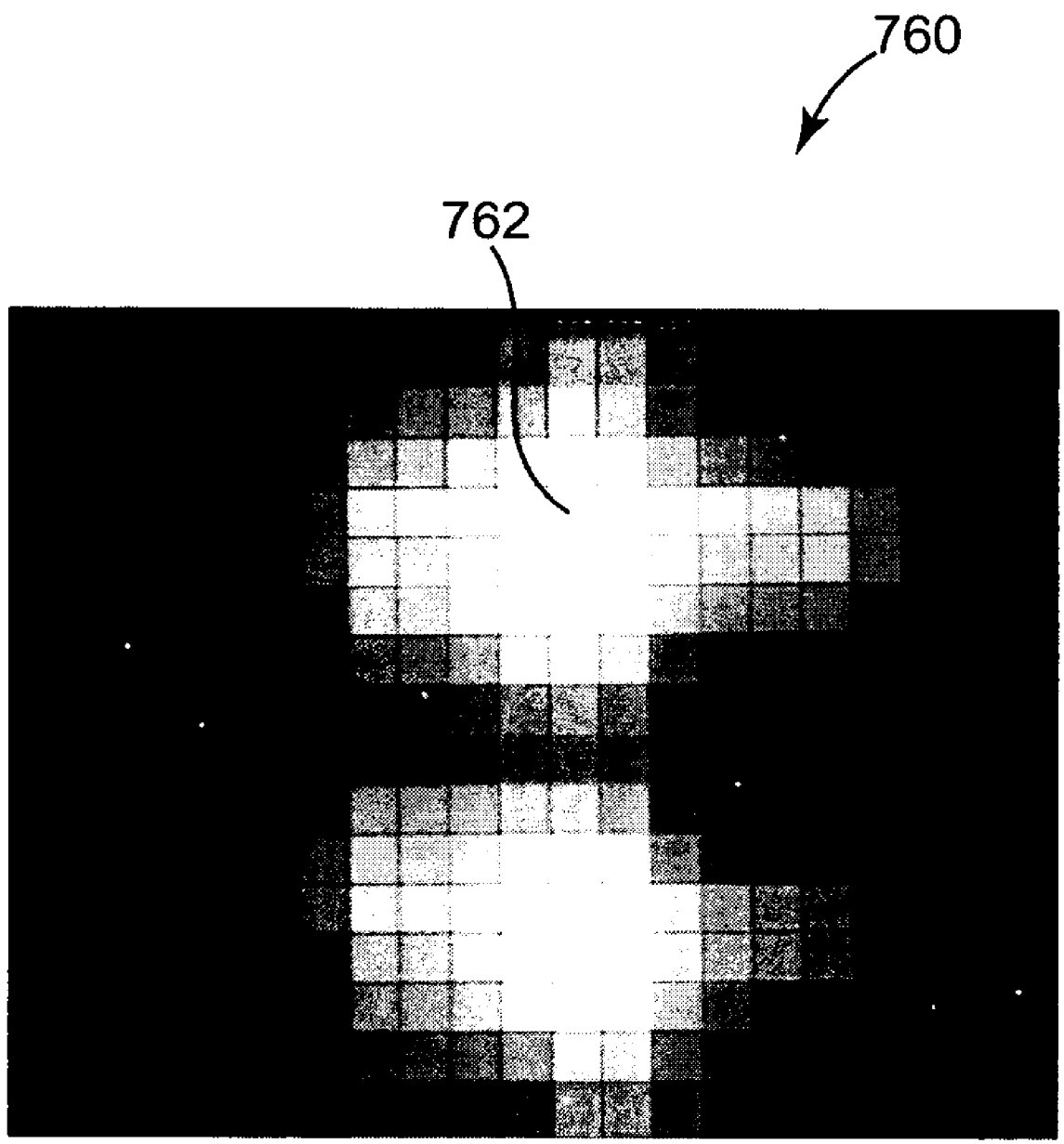
FIG. 13 is an image obtained by an inspection system illustrating one embodiment of a sample point.

FIG. 13 is an image 760 obtained by inspection system 104 illustrating one embodiment of one sample point 740. Image 760 is analyzed by analysis system 110 to determine parameters relating to exposure tool 120 and/or inspection system 104. Each portion of image 760, such as portion 762, corresponds to a relief image of sample point 740 patterned on the surface of BPG sample 106. Each portion of image 760 corresponds to a component A-P of array 400 and a focus step.

The illuminance of each portion of image 760 varies based on the depth of each relief image of sample point 740 of BPG sample 106. The illuminance of each portion increases in response to a larger depth of the relief image patterned on the surface of BPG sample 106 and decreases in response to a smaller depth of the relief image patterned on the surface of BPG sample 106.

In one embodiment, inspection system 104 obtains images including a single sample point 740, such as image 760. In another embodiment, inspection system 104 obtains multiple images per sample point 740 that are combined together to provide an image, such as image 760, of a single sample point 740. Inspection system 104 may obtain multiple images per sample point 740 if the magnification of objective 164 is too high, such that only part of a sample point 740 is in the field of view of objective 164. Using a high magnification and combining the images to produce an image, such as image 760, of a single sample point 740 is useful for analyzing smaller structures. Smaller structures are generated as the pitch or grating period of components A-P of blazed phase grating array 400 is reduced, resulting in the diffraction angle becoming smaller. The magnification or the numerical aperture of objective 164 can be changed to collect images of the smaller structures.

In another embodiment, each image collected by inspection system 104 includes multiple sample points 740. In one embodiment, inspection system 104 is a macro inspection tool that obtains a single image of the entire BPG sample 106. In this case, where each image collected by inspection system 104 includes multiple sample points 740, the image is divided to provide multiple images, such as image 760, where each image includes a single sample point 740. The process of either combining or dividing images collected by inspection system 104 is performed by either inspection system 104 or analysis system 110. As previously described above, each image, such as image 760, of each sample point 740 is given a unique name according to the predefined sequential naming protocol to link the image to the sample point location on BPG sample 106. The images obtained by inspection system 104 are then analyzed by inspection system 104 or stored in memory 182 (FIG. 4) for analysis by analysis system 110.

Analysis system 110 automatically or upon the request of a user retrieves the images saved by inspection system 104. For each image, analysis system 110 uses an edge detection process to pre-align the images within the analysis space. Analysis system 110 then converts the image data, such as illuminance, color, hue, or saturation values of the images to intensity values as a function of predefined pixel locations to determine intensity gradients. The predefined pixel locations represent the azimuthal angle and focus steps for the entire analysis space.

Analysis system 110 analyzes the intensity values as a function of focus step for each of the azimuthal angles and blazed phase grating array 400 pitches or grating periods. In one embodiment, the intensity values are fit to a predefined polynomial. Best focus by azimuth is determined by calculating the derivative of the polynomial to determine the inflection points. In a two beam interferometer, the maximum point is the best focus by azimuth. In another embodiment, he best focus by azimuth is determined by finding the maximum intensity value for each azimuth or the largest physical relief depth for each azimuth. From the best focus data, exposure field parameters are determined and/or aberration analysis is performed. Focus, average focus across a particular value, scan direction, focal plane deviation, tilt coefficients, and other parameters can be determined.

Aberration analysis takes the Fourier transform of the best focus data and then determines the harmonics from the Fourier transform. The focus delta associated with a harmonic is equal to the aberration coefficient for that harmonic. The harmonics are associated through the Zernike polynomials. Therefore, the associated aberration polynomial is determined based on the best focus delta for the harmonic of interest. The aberration values are determined by sample point across BPG sample 106. The aberration values are then analyzed as subsets of predefined variables of interest, such as the entire BPG sample 106 or exposure fields of BPG sample 106. In one embodiment, the aberration values are analyzed with respect to scan direction or any other suitable components of interest of BPG sample 106 as defined by the user.

Figure 14:
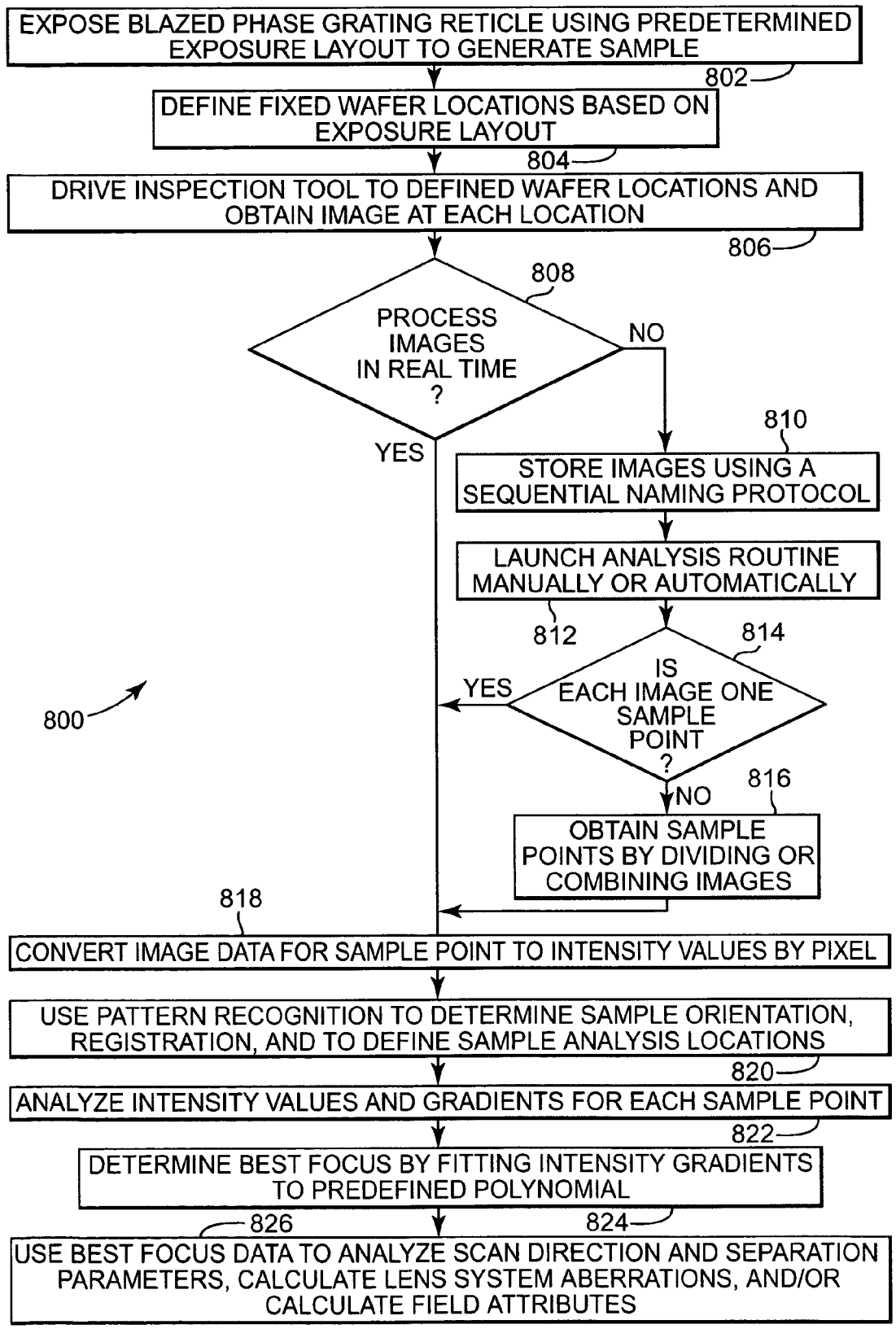
FIG. 14 is a flow diagram illustrating one embodiment of a method for analyzing images of sample points of a BPG sample for determining parameters for an exposure tool and/or inspection system.

FIG. 14 is a flow diagram 800 illustrating one embodiment of a method for analyzing images, such as image 760, of sample points 740 of BPG sample 106 for determining parameters of exposure tool 120 and/or inspection system 104. At 802, a BPG reticle including at least one blazed phase grating array 400 is exposed in exposure tool 120 to generate a BPG sample 106 based on a predefined exposure field layout, such as exposure field layout 700 (FIG. 10). In one embodiment, the BPG reticle includes a plurality of blazed phase grating arrays 400 each having a different grating pitch. At 804, sample point 740 locations on BPG sample 106 are determined based on the exposure field layout for BPG sample 106. At 806, BPG sample 106 is placed on stage 168 of inspection system 104 and controller 150 of inspection system 104 drives inspection system 104 to the defined sample point 740 locations. Imaging system 156 of inspection system 104 obtains images of each sample point 740.

At 808, if the images are to be processed in real time, control passes to block 818. If the images are not to be processed in real time, control passes to block 810. At 810, the images are stored using the sequential naming protocol linking each image to a sample point location on BPG sample 106. At 812, the analysis routine of analysis system 110 is launched automatically or manually. In one embodiment, the analysis routine is launched automatically in response to a message provided by inspection system 104, in response to the presence of the stored images, or in response to another suitable indicator. In one embodiment, the analysis routine is launched manually by a user through user interface 192 of analysis system 110, through a user communicating with analysis system 110 through network interface 190, or through another suitable manual indicator provided by a user.

At 814, if each image includes a single sample point 740, control passes to block 818. If each image includes less than a single sample point 740 or more than a single sample point 740, then control passes to block 816. At 816, images of single sample points 740 are obtained by combining multiple adjacent images including less than a single sample point 740, or by dividing images including more than a single sample point 740. At 818, the image data, such as illuminance data, color data, hue data, saturation data, or other suitable image data, for sample point 740 is converted to intensity values by pixel.

At 820, pattern recognition is used to determine sample point 740 orientation and registration, and to define the sample point 740 location on BPG sample 106. In one embodiment, the orientation and registration of sample point 740, and the defining of the sample point 740 location on BPG sample 106 is completed before the image data for sample point 740 is converted to intensity values by pixel.

At 822, the intensity values and the gradients are analyzed for each sample point 740. At 824, the best focus by azimuth is determined by fitting the intensity gradient values to a predefined polynomial. At 826, the best focus data is used to analyze scan direction and separation parameters, calculate lens system aberrations, and/or calculate field attributes for exposure tool 120. In one embodiment, the best focus data is used to analyze the illumination parameters of inspection system 104.

Figure 15:
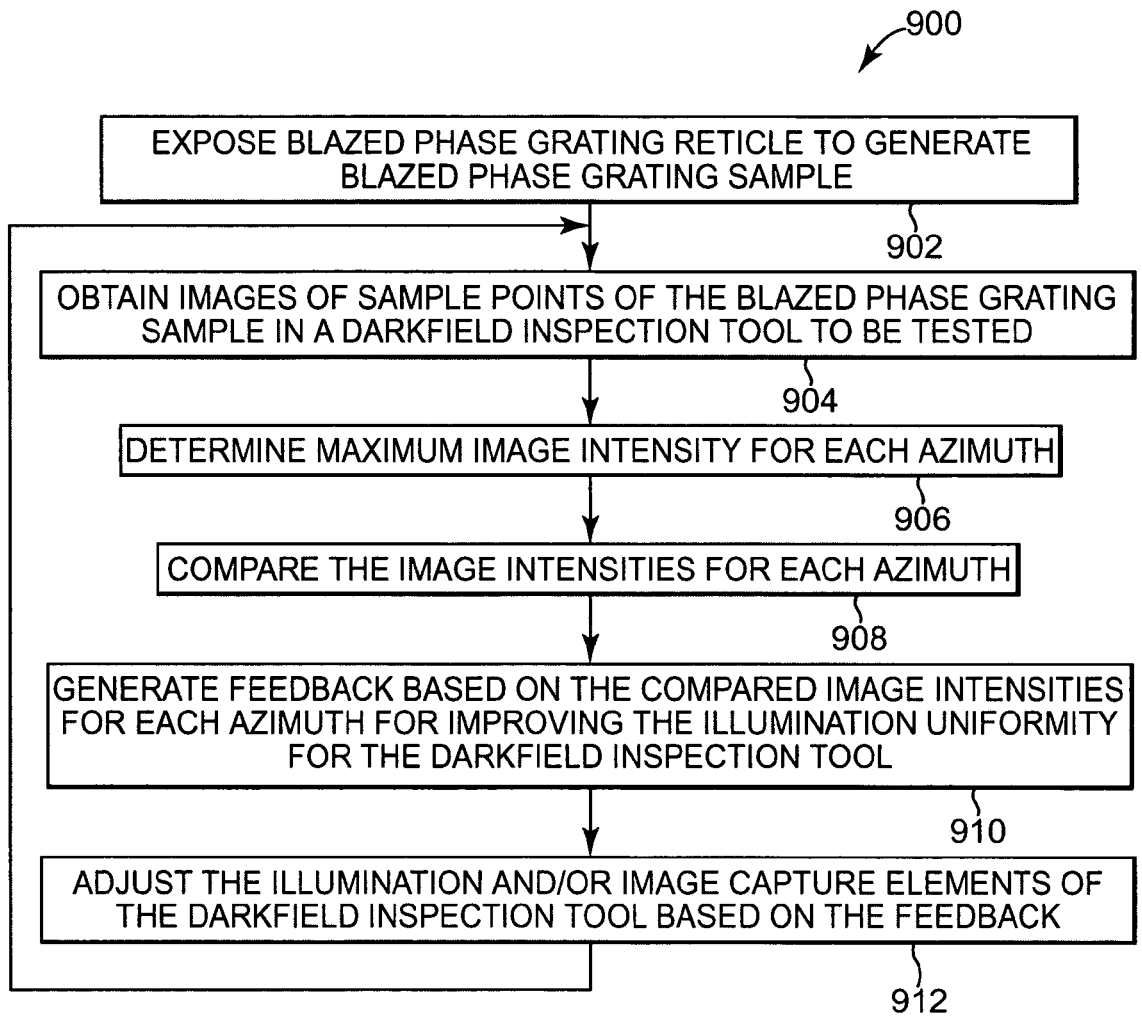
FIG. 15 is a flow diagram illustrating one embodiment of a method for optimizing light path uniformity in a defect inspection system.

One embodiment for analyzing images of blazed phase grating samples includes optimizing the light path uniformity in an inspection system, such as inspection system 104. FIG. 15 is a flow diagram illustrating one embodiment of a method 900 for optimizing light path or illumination uniformity in inspection system 104. At 902, a blazed phase grating reticle is exposed in exposure tool 120 to generate a BPG sample 106. At 904, inspection system 104 obtains images of sample points of BPG sample 106 in a darkfield mode.

At 906, the maximum image intensity for each azimuth of each sample point is determined by inspection system 104 or analysis system 110. In one embodiment, the maximum image intensity data is compared to previously stored data for the same hardware set to determine the effect of any changes made to optical paths of inspection system 104. At 908, the image intensities for each azimuth within the sample point are compared. At 910, inspection system 104 or analysis system 110 generates feedback based on the compared image intensities for each azimuth for improving the illumination uniformity of inspection system 104. At 912, the illumination and/or image capture elements of inspection tool 104 are adjusted based on the feedback. Imaging system 156, illumination source 170, and/or illumination beam steering components 160 or 162 are adjusted to improve the illumination uniformity of inspection system 104 based on the feedback. Control then returns to block 904 for obtaining additional images of BPG sample 106 and the process is repeated if desired until the optimal illumination uniformity is achieved. In one embodiment, blocks 902-912 are initiated or performed manually as desired. Adjustments to hardware settings or hardware designs can be manually performed based on the feedback. Manual adjustments to controller 150 affected settings can also be performed, such as changes due to temperature, electrical current, or electromechanical settings. In another embodiment, blocks 902-912 are performed automatically without user intervention.

Referring back to FIG. 13 of image 760 of a sample point 740, the illuminance of image 760 varies from left to right and from top to bottom. The highest illuminance is obtained from the deepest relief pattern of BPG sample 106 such that image 760 is brightest in the middle in this embodiment. If the darkfield illumination and image collection pathways of inspection system 104 were pure and the relief images for BPG sample 106 have all the same maximum intensities or relief depths, then there would be no variation in the maximum brightness for each row of image 760. The dark bands in image 760 are due to obscurations or optically variant materials in the illumination pathway or the image collection pathway of inspection system 104. By analyzing these images, the illumination and/or image capture elements of inspection system 104 can be modified and the test performed again to improve the illumination uniformity of inspection system 104.

A BPG sample 106 can be used to analyze the entire illumination pathway and pupil space of inspection system 104. The illumination and image uniformity of inspection system 104 in the darkfield inspection mode can be measured and described. The process can be used for any darkfield imaging system, such as those used in microscopes, defect inspection tools, and darkfield alignment tools, such as steppers and scanners. By optimizing the darkfield illumination and imaging uniformity, the sensitivity, acuity, and accuracy of the inspection system can be improved.

Figure 16:
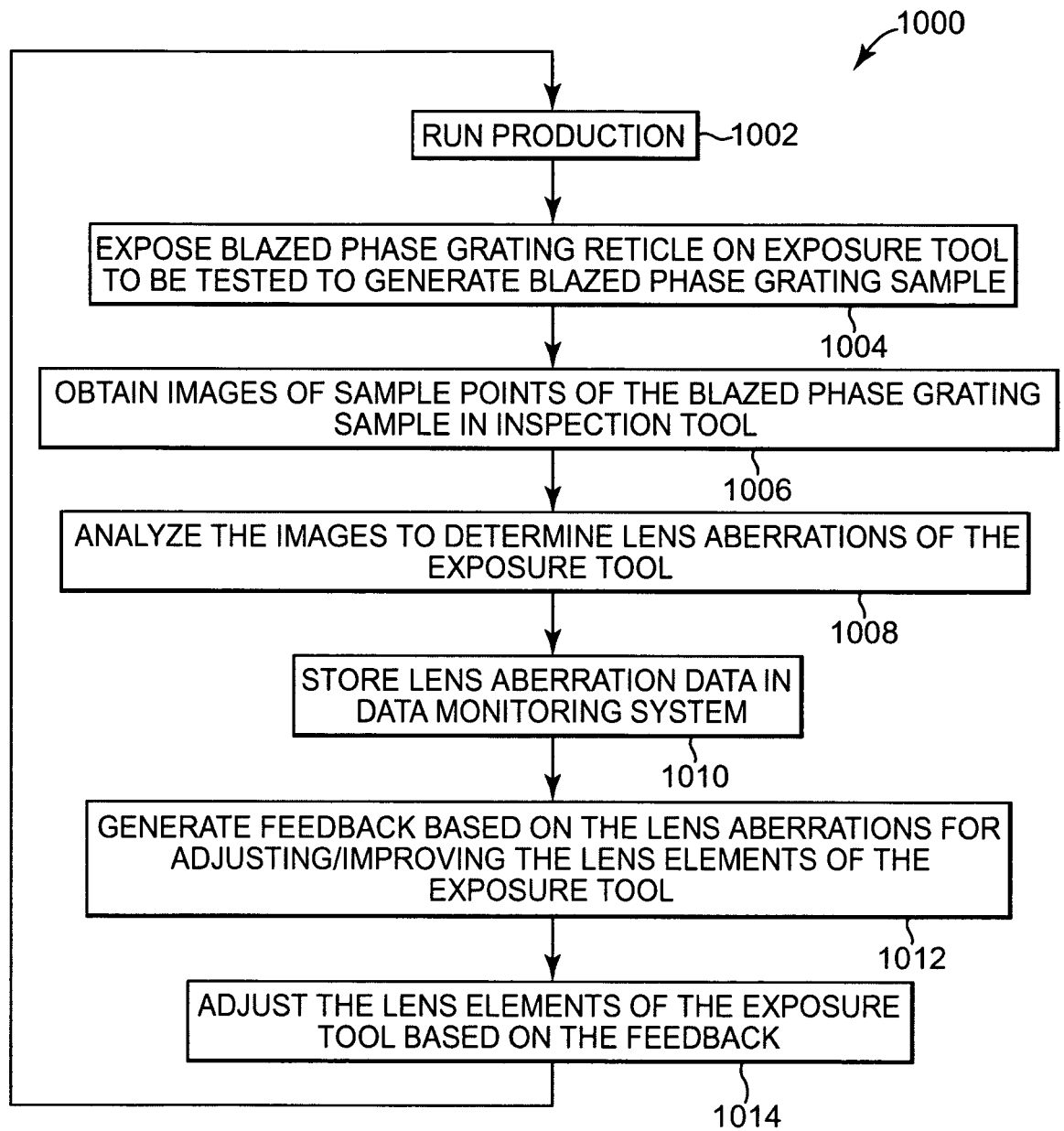
FIG. 16 is a flow diagram illustrating one embodiment of a method for controlling lens system aberrations from run to run.

Another embodiment for analyzing images of blazed phase grating samples includes run to run control for lens system aberrations of an exposure tool, such as exposure tool 120. FIG. 16 is a flow diagram illustrating one embodiment of a method 1000 for controlling lens system aberrations from run to run. At 1002, normal production is run on exposure tool 120. At 1004, a blazed phase grating reticle is exposed on exposure tool 120 to generate a BPG sample 106. At 1006, inspection system 104 obtains images of sample points 740 of BPG sample 106. At 1008, inspection system 104 or analysis system 110 analyzes the images to determine lens system aberrations in lens system 136 of exposure tool 120. At 1010, the lens system aberration data is stored in a data monitoring system. In one embodiment, the data monitoring system is part of analysis system 110. In one embodiment, the data monitoring system allows review or monitoring of current and historical data (i.e. statistical process control, advanced process control, fault detection system, etc.).

At 1012, inspection system 104 or analysis system 110 generates feedback based on the determined lens system aberrations for adjusting and/or improving the lens elements, such as lens elements 144, of exposure tool 120. At 1014, controller 124 of lithography cell 102 adjusts the lens elements, such as lens elements 144, of lens system 136 based on the feedback from inspection system 104 or analysis system 110. The lens elements, such as lens elements 144, of lens system 136 are adjusted by using the feedback response to adjust control algorithms defining the response of lens system 136. In one embodiment, lens system 136 is adjusted to compensate for tilt, coma, astigmatism, three fold, four fold, and/or five fold. In one embodiment, blocks 1002-1014 are initiated or performed manually as desired. In another embodiment, blocks 1002-1014 are performed automatically without user intervention on a scheduled basis, such as once a day, once a week, twice a month, etc.

Lens system 136 is adjusted and maintained from run to run to compensate for changes in lens system 136 aberrations over time or for the effect of the aberrations on particular features being printed. This method provides a non-intrusive method for periodically measuring lens system 136 aberrations to prevent lens system 136 aberrations from drifting from run to run. In addition, lens elements 144 of lens system 136 can be adjusted quickly based on the periodic measurements without severely disrupting the normal production schedule for exposure tool 120. The run to run control for lens system aberrations provided by using blazed phase grating samples provides a non-intrusive, efficient, cost effective, accurate, and precise method for controlling lens system aberrations over time.

Figure 17:
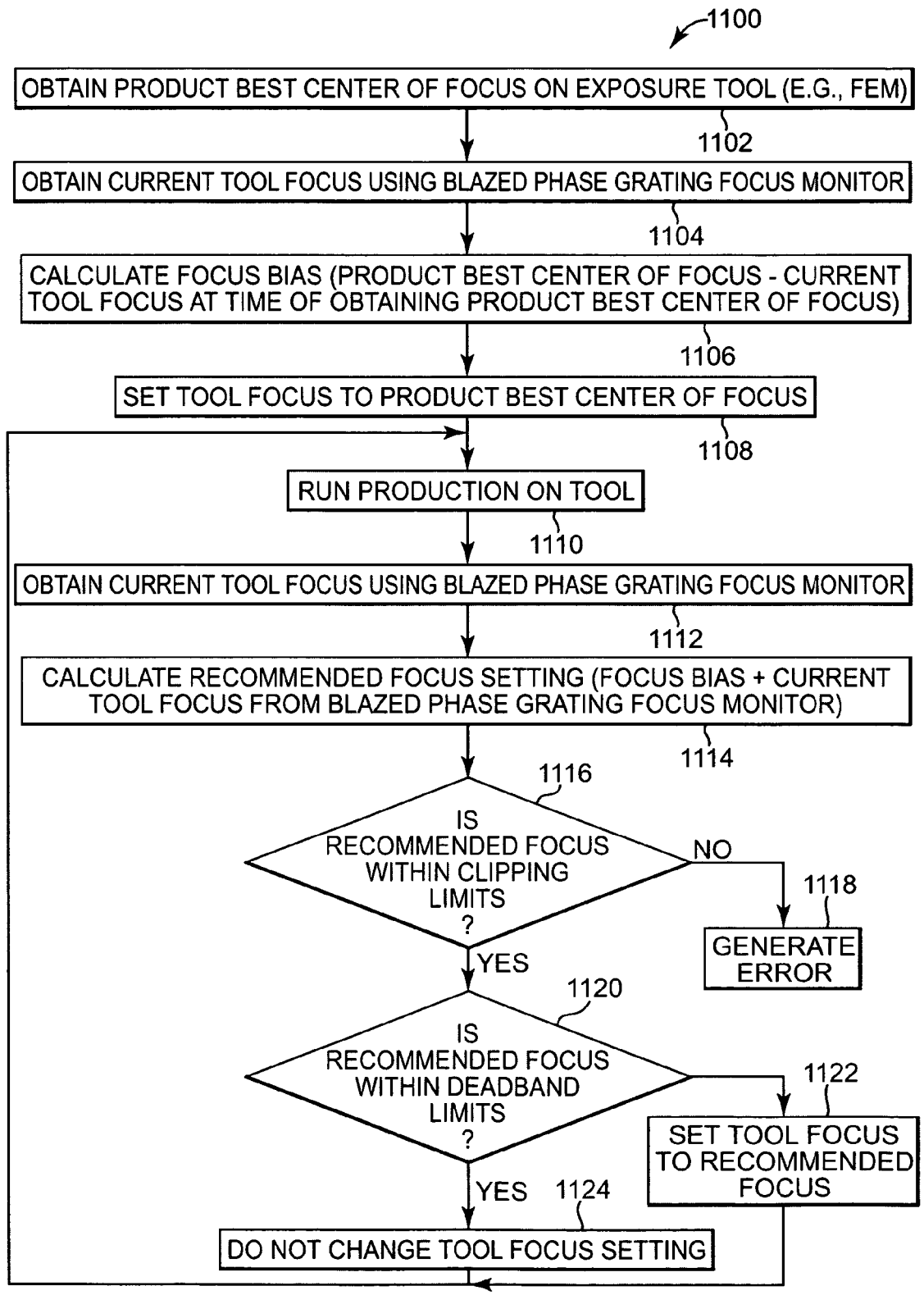
FIG. 17 is a flow diagram illustrating one embodiment of a method for automatically adjusting the focus of an exposure tool.

Another embodiment for analyzing images of blazed phase grating samples includes providing focus feedback to an exposure tool, such as exposure tool 120. FIG. 17 is a flow diagram illustrating one embodiment of a method 1100 for manually or automatically adjusting the focus of exposure tool 120 based on run to run focus feedback. The method is applied to each product/tool/layer/reticle context value combination run on exposure tool 120. At 1102, the product best center of focus on exposure tool 120 is obtained. In one embodiment, the product best center of focus is obtained by using a Focus Exposure Matrix (FEM) or other suitable method. At 1104, the current tool focus using a blazed phase grating focus monitor measurement is obtained. In one embodiment, the current tool focus is obtained using another suitable method. As used herein, a blazed phase grating focus monitor measurement is defined as the process of generating a blazed phase grating sample on an exposure tool and determining the focus of the exposure tool based on the best focus values by sample point. In one embodiment, the best focus value of a sample point is the average of the best focus by azimuth of the sample point. The current tool focus is obtained using the methods described above where the average of the best focus values by sample point across the blazed phase grating sample is the current tool focus value.

At 1106, the focus bias or delta baseline is calculated by exposure tool 120 or analysis system 110. The focus bias equals the product best center of focus minus the current tool focus at the time of obtaining the product best center of focus. At 1108, the current focus of exposure tool 120 is set to the product best center of focus. At 1110, normal production of the selected product/tool/layer/reticle context value combination is run on exposure tool 120. At 1112, the current tool focus using the blazed phase grating focus monitor or another suitable method is obtained again. In one embodiment, the current tool focus is obtained manually. In another embodiment, the current tool focus is obtained automatically based on a schedule, such as once a day, once a week, twice a month, etc. In one embodiment, the current tool focus measurement passes through a Statistical Process Control (SPC), and a filter to verify that the measured focus meets a certain confidence level.

At 1114, the recommended focus setting for exposure tool 120 is calculated. The recommended focus setting equals the focus bias plus the current tool focus from the blazed phase grating focus monitor. At 1116, exposure tool 120 or analysis system 110 determines whether the recommended focus is within clipping limits. Exposure tool 120 or analysis system 110 determines that the recommended focus is within clipping limits by determining if the product best center of focus minus the clipping limit is less than the recommended focus, and the recommended focus is less than the product best center of focus plus the clipping limit. The clipping limit tests whether the recommended focus is within expected limits. In one embodiment, the clipping limit is 0.15 or another suitable value. If the recommended focus is not within the clipping limits, then at 1118 an error is generated to inform a user and production on exposure tool 120 is stopped. In one embodiment, production on exposure tool 120 continues, but the recommended focus is clipped by the clipping limit.

If the recommend focus is within the clipping limits, then at 1120, exposure tool 120 or analysis system 110 determines whether the recommended focus is within the deadband limits. Exposure tool 120 or analysis system 110 determines that the recommended focus is within the deadband limits by determining if the product best center of focus minus the deadband limit is less than the recommended focus, and the recommended focus is less than the product best center of focus plus the deadband limit. The deadband limits keep exposure tool 120 or analysis system 110 from overcompensating for focus changes if the recommended focus is within the noise of the blazed phase grating focus monitor measurement. In one embodiment, the deadband limit is 0.03 or another suitable value.

If the recommended focus is within the deadband limits, then at 1124 the focus of exposure tool 120 is not changed. If the recommended focus is not within the deadband limits, then at 1122 the focus of exposure tool 120 is set to the recommended focus. Control then returns to block 1110 where normal production is run on exposure tool 120 and the process is repeated on a desired schedule. In one embodiment, blocks 1110-1124 are initiated or performed manually as desired. In another embodiment, blocks 1110-1124 are preformed on a regular basis automatically without user intervention.

Method 1100 provides run to run focus feedback to exposure tool 120. Any focus drifts of exposure tool 120 can be discovered and corrected before the focus drifts result in exposure tool 120 producing product having critical dimensions out of tolerance. The current method provides a cost effective, efficient, accurate, and precise run to run focus feedback method that does not negatively impact the normal production schedule of the exposure tool.

In addition to the described run to run focus feedback and run to run control for lens system aberrations embodiments, other embodiments analyze images of blazed phase grating samples to provide feed forward or feedback to control other portions of lithography cell 102 and/or inspection system 104. For example, in one embodiment analyzing BPG samples 106 provides feedback for optimizing exposure tool 120 for specific product layer features based on the effect of lens system aberrations on the specific product layers features.

Figure 18:
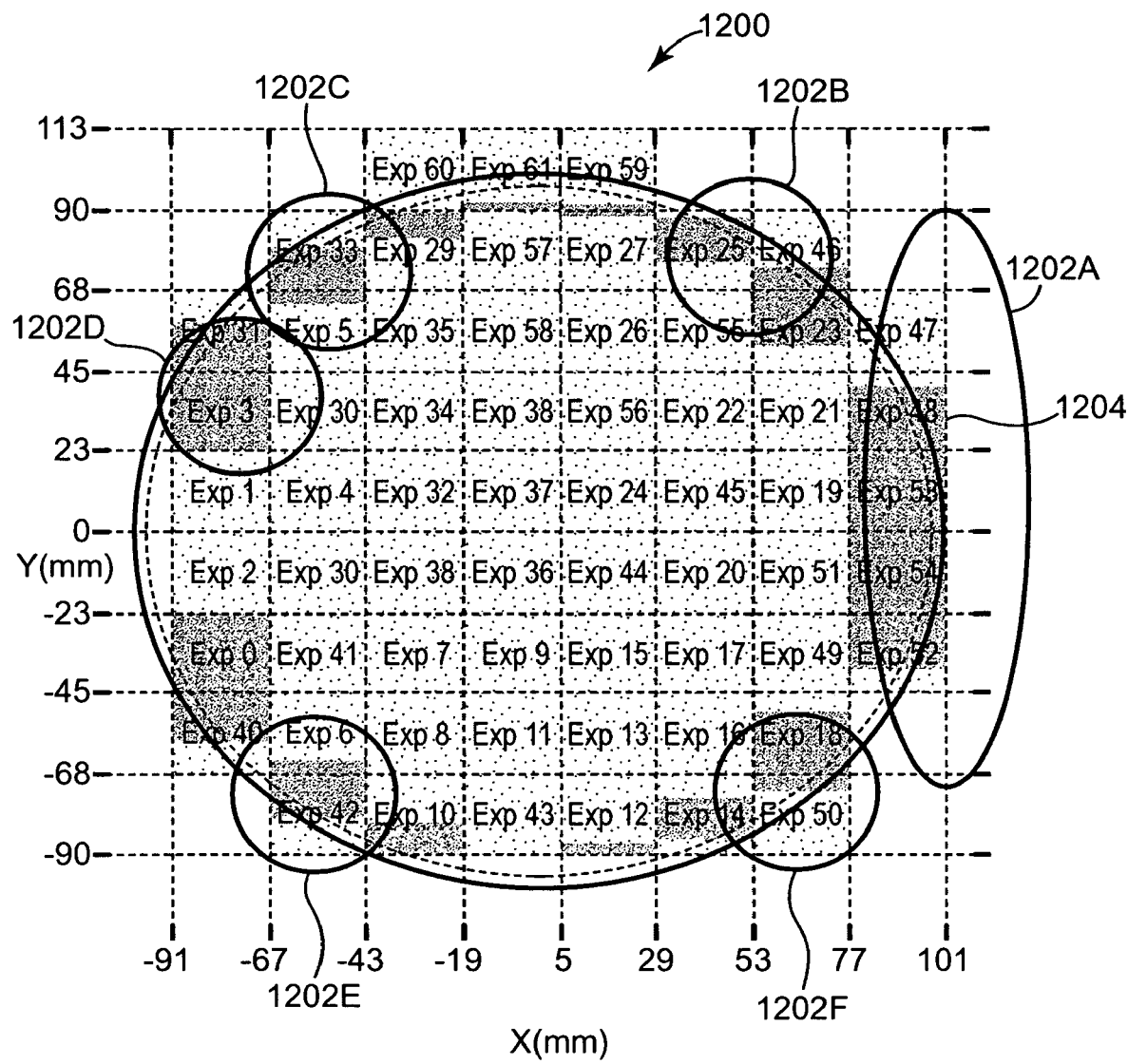
FIG. 18 is a diagram illustrating one embodiment of a product shot map.

Another embodiment for analyzing images of blazed phase grating samples includes using blazed phase grating focus monitor measurements for describing the best focus by position within an image field and across a wafer. FIG. 18 is a diagram illustrating one embodiment of a product shot map 1200. Product shot map 1200 includes a plurality of exposure fields, such as exposure field 1204. Focus sensors 146 of exposure tool 120 adjust the focus of exposure tool 120 during the exposure of each exposure field. Encircled exposure fields 1202A-1202F, include wafer edge regions where focus sensors 146 are not fully operational due to some of the focus sensors 146 sensing outside the edge of the wafer or in a deadband near the edge of the wafer. In regions 1202A-1202F, exposure tool 120 uses focal plane fitting data from adjacent exposure fields to make a best guess approximation for the focus settings for regions 1202A-1202F based on focal plane fitting models. Often times, these best guess focal plane fitting models do not accurately describe the wafer edge.

Figure 19:
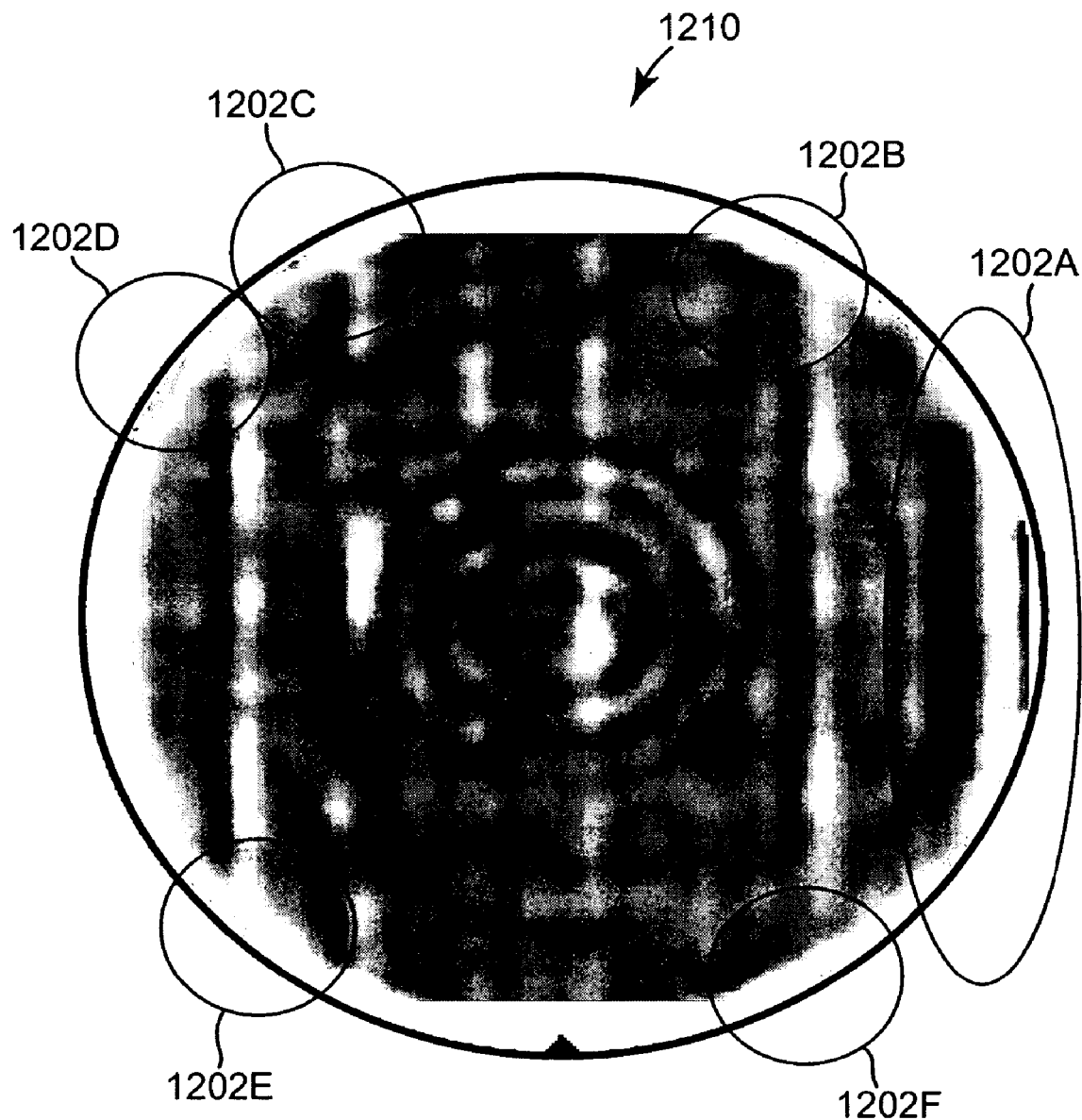
FIG. 19 is a diagram illustrating one embodiment of a mathematical representation of best focus values by sample point across a blazed phase grating sample generated using the product shot map of FIG. 18.

FIG. 19 is a diagram illustrating one embodiment of a mathematical representation 1210 of best focus values by sample point across a BPG sample 106 generated using product shot map 1200. The blazed phase grating reticle is bladed down and exposed using the same exposure and step and scan routing routines as the product for product shot map 1200 to generate BPG sample 106. Images of samples points 740 of BPG sample 106 are obtained by inspection system 104. Analysis system 110 analyzes the images to determine the best focus by sample point 740 across BPG sample 106. In one embodiment the best focus of sample point 740 is the average of the best focus by azimuth for sample point 740. Mathematical representation 1210 includes regions 1202A-1202F where the best guess focus settings do not coincide with the actual measured best focus values from BPG sample 106. The best focus values by sample point 740 determined from BPG sample 106 are used to adjust the focus offsets by shot of exposure tool 120 to improve the focus setting in regions 1202A-1202F.

Figure 20:
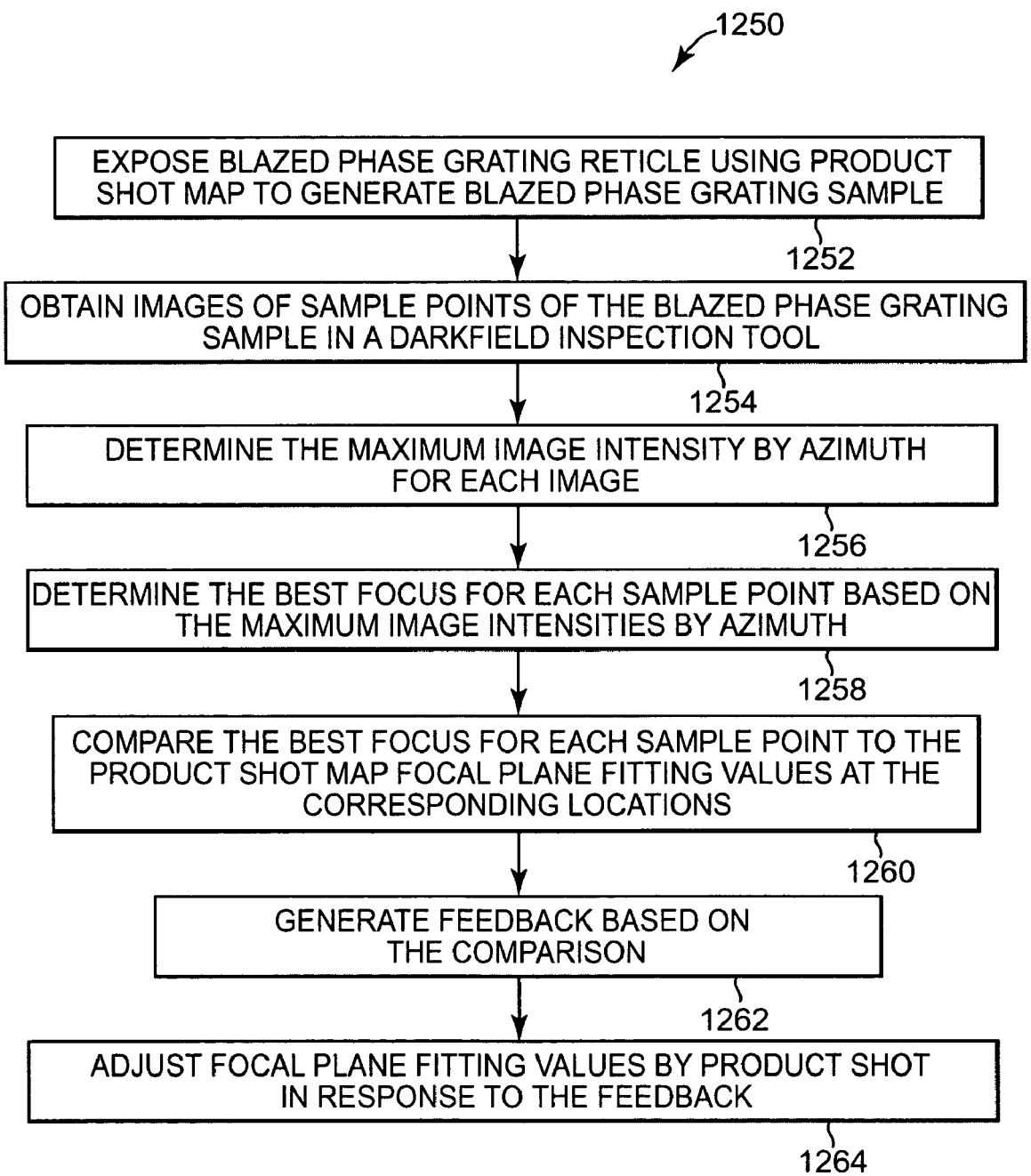
FIG. 20 is a flow diagram illustrating one embodiment of a method for optimizing the focal plane fitting functions for an image field on a substrate.

FIG. 20 is a flow diagram illustrating one embodiment of a method 1250 for optimizing the focal plane fitting functions for an image field on a substrate. At 1252, the BPG reticle is exposed using the product shot map, such as product shot map 1200, to generate a BPG sample 106. At 1254, BPG sample 106 is inspected in inspection system 104 to obtain images of sample points 740 of BPG sample 106 across the entire BPG sample 106. In one embodiment, up to 3000 images for a 200 mm diameter wafer are obtained. In other embodiments, any suitable number of images are obtained.

At 1256, analysis system 110 determines the maximum intensity by azimuth for each image of each sample point 740. At 1258, analysis system 110 determines the best focus for each sample point 740 based on the maximum image intensities by azimuth for each image. At 1260, analysis system 110 compares the best focus values across BPG sample 106 to the product shot map focal plane fitting values at the corresponding locations. At 1262, analysis system 110 generates feedback based on the comparison of the best focus values to the product shot map focal plane fitting values. At 1264, the focal plane fitting values, such as focus offsets and tilt, of exposure tool 120 are adjusted by product shot based on the feedback to improve the focal plane fitting for the product exposure fields and correct for the inaccuracies of focus sensors 146.

Method 1250 provides a method to measure and describe the optimal focus plane fitting functions for any image field on a substrate. Measured offsets to the predicted values applied by the exposure tool are applied to produce the best plane fit for the product. The blazed phase grating focus monitor describes the best focus by position within an image field and across a wafer. The process uses the act of focus control mechanisms of exposure tool 120 in a manner similar to that used during standard product exposures. The final focus offset and tilt values are measured to a high degree of accuracy and precision as a function of the interaction of the exposure tool focus system, product layout map, and substrate topography. This allows the determination of the lack of fit of between the exposure tool determined optical focal plane and the resultant printed focal plane. The difference is due to the inability of the exposure tool to accurately measure and apply the best image field focal plane. Based on the lack of fit between the best guess applied focal plane and the actual focal plane, the differences to the image field parameters by shot are adjusted where appropriate. This results in a truer image plane and better critical dimension control across the affected exposure fields.

Another embodiment for analyzing images of blazed phase grating samples includes using the preparation of BPG samples 106 to determine illumination parameters of exposure tool 120. In one embodiment, BPG sample 106 is generated by exposure tool 120 using a BPG reticle and exposure field layout designed to provide sample points 740 that when analyzed provide information from which the illumination parameters of exposure tool 120 are determined. In one embodiment, the numerical aperture and/or sigma of exposure tool 120 are determined. In another embodiment, the telecentricity, ellipticity, and/or the shape of the illumination source are determined. In another embodiment, the reticle flatness, reticle movement (for scanners), chuck profile, and/or chuck flatness are determined. In another embodiment, variations due to the heating of lens elements are monitored. In another embodiment, wafer and reticle stage repeatability and/or stage movement parameters are determined.

Another embodiment for analyzing images of blazed phase grating samples includes using BPG samples 106 to analyze and optimize material process parameters. In one embodiment, the topography of a wafer is monitored to determine the effects of different materials or processes, such a chemical mechanical polishing, etching, deposition processes, etc. In another embodiment, the effect of changes to the material constant of the BPG photoresist or to the underlying materials is determined to examine opacity, planarity, etc.

In another embodiment, inspection system 104 is used to inspect BPG samples 106 generated by exposure tool 120 to determine degree of polarization, polarization form (tangential or linear polarization), and polarization uniformity across the slit and across the scan of the illumination source in the exposure field.

Embodiments of the present invention provide a low cost, efficient, and accurate system and method for analyzing images of BPG samples to determine parameters of exposure tools and/or inspection systems. Exposure tool parameters, such as scan direction, field attributes, field plane fitting effects, across scan effects, across slit effects, across field effects, wafer level effects, and lens system aberrations including single structure or multiple structure angle analysis can be performed with little interruption of the normal manufacturing process. The BPG sample can be exposed using many different protocols for detecting various effects, such as the edge of the wafer, the focus sensor system, the response to local variations, the lens across the slit, the mechanical effects of the scanning stage, etc.

In addition, the BPG sample can be generated and images of the BPG sample captured in an inspection system without severely disrupting the normal manufacturing process. For example, in one embodiment, a BPG sample including four exposure fields with 88 sample points per field for a total of 352 sample points can be exposed in about 10 minutes on an exposure tool and inspected in about six minutes on an inspection system to obtain the images of the 352 sample points. The images of the 352 sample points can be quickly and automatically analyzed by the analysis system to determine parameters of the exposure tool and/or the inspection system.

What is claimed is:

1. An inspection system comprising:
   an illumination source configured to illuminate a blazed phase grating sample comprising relief gratings at a plurality of angles and relief depths, each relief grating angle adapted to direct light through a different azimuth of a pupil of the inspection system;
   image collection pathways and an imaging system configured to capture an image of a sample point of the blazed phase grating sample; and
   a controller configured to adjust the illumination source in response to an analysis of the image of the sample point to determine illumination uniformity of the inspection system, the analysis being based on a comparison of maximum image intensities for each azimuth.

2. The inspection system of claim 1, further comprising:
   a beam steering component configured to steer light from the illumination source to the blazed phase grating sample,
   wherein the controller is configured to adjust the beam steering component in response to the analysis of the image of the sample point.

3. The inspection system of claim 1, wherein the controller is configured to adjust the imaging system m response to the analysis of the image of the sample point.

4. The inspection system of claim 1, wherein the controller is configured to adjust the image collection pathways in response to the analysis of the image of the sample point.

5. The inspection system of claim 1, wherein the illumination source is configured to illuminate the blazed phase grating sample in a darkfield inspection mode.

6. The inspection system of claim 1, wherein the controller is configured to perform the analysis of the image of the sample point.

7. An inspection system comprising:
   means for providing a blazed phase grating sample configured to reflect light through a plurality of azimuths of a pupil of an inspection system;
   means for obtaining an image of a sample point of the blazed phase grating sample in the inspection system;
   means for analyzing the image to determine illumination uniformity of the inspection system; and
   means for adjusting the inspection system based on the analysis to optimize the illumination uniformity of the inspection system;
   wherein the means for analyzing the image comprises:
      means for determining a maximum image intensity for each azimuth;
      means for comparing the maximum image intensities; and
      means for generating feedback based on the comparison for adjusting the inspection system.

8. A method for optimizing the illumination uniformity of an inspection system, the method comprising:
   providing a blazed phase grating sample configured to reflect light through a plurality of azimuths of a pupil of an inspection system;
   obtaining an image of a sample point of the blazed phase grating sample in the inspection system;
   analyzing the image to determine illumination uniformity of the inspection system; and
   adjusting the inspection system based on the analysis to optimize the illumination uniformity of the inspection system;
   wherein analyzing the image comprises:
      determining a maximum image intensity for each azimuth;
      comparing the maximum image intensities; and
      generating feedback based on the comparison for adjusting the inspection system.

9. The method of claim 8, further comprising:
   comparing the illumination uniformity of the inspection system to a previously obtained illumination uniformity of the inspection system to determine an effect of adjusting the inspection system based on the analysis.

10. The method of claim 8, wherein providing the blazed phase grating sample comprises exposing a blazed phase grating reticle including at least one array of blazed phase gratings in an exposure tool.

11. The method of claim 8, wherein adjusting the inspection system comprises adjusting an illumination source of the inspection system.

12. The method of claim 8, wherein adjusting the inspection system comprises adjusting an illumination beam steering component of the inspection system.

13. The method of claim 8, wherein adjusting the inspection system comprises adjusting an image capture element of the inspection system.

14. A method for optimizing the light path uniformity of an inspection system, the method comprising:
   providing a blazed phase grating sample comprising relief gratings at a plurality of angles and relief depths, each relief grating angle adapted to direct light though a different azimuth of a pupil of the inspection system;

obtaining an image of the sample in an inspection system;

analyzing the image to determine a maximum image intensity for each azimuth;

comparing the maximum image intensities for each azimuth;

providing feedback to the inspection tool based on the comparison; and adjusting an illumination element of the inspection system based on the feedback.

15. The method of claim 14, wherein adjusting an illumination element comprises adjusting one of an illumination source and an illumination beam steering component.

16. The method of claim 14, further comprising:
adjusting an image capture element of the inspection tool based on the feedback.

17. The method of claim 16, wherein adjusting an image capture element comprises adjusting one of an objective and an imaging system.

* * * * *